United States Patent
Arcediano et al.

(10) Patent No.: US 11,927,585 B2
(45) Date of Patent: Mar. 12, 2024

(54) SOLVENT-BASED INKS AND COATINGS FOR FOOD CONTACT APPLICATIONS

(71) Applicant: SUN CHEMICAL CORPORATION, Parsippany, NJ (US)

(72) Inventors: Sandra Arcediano, Vizcaya (ES); Jose Ramon Maeso, Vizcaya (ES); Egidio Scotini, Florence (IT); Michael Simoni, Yorkshire (GB)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 18/024,218

(22) PCT Filed: Sep. 22, 2021

(86) PCT No.: PCT/ES2021/070689
§ 371 (c)(1),
(2) Date: Mar. 1, 2023

(87) PCT Pub. No.: WO2022/064090
PCT Pub. Date: Mar. 31, 2022

(65) Prior Publication Data
US 2023/0243805 A1 Aug. 3, 2023

Related U.S. Application Data

(60) Provisional application No. 63/081,440, filed on Sep. 22, 2020.

(51) Int. Cl.
*G01N 33/32* (2006.01)
*A23L 5/42* (2016.01)
(Continued)

(52) U.S. Cl.
CPC ............ *G01N 33/32* (2013.01); *A23L 5/42* (2016.08); *C09D 11/322* (2013.01); *C09D 11/36* (2013.01); *C09D 11/40* (2013.01)

(58) Field of Classification Search
CPC ........ G01N 33/32; G01N 21/251; A23L 5/40; C09D 11/322; G01J 3/501; G01J 3/463
See application file for complete search history.

(56) References Cited

U.S. PATENT DOCUMENTS 5,255,350 A * 10/1993 Hermann ................ B01F 33/84
358/1.9
9,649,868 B2 * 5/2017 Simoni .................... G03F 3/10
(Continued)

FOREIGN PATENT DOCUMENTS

| EP | 3 260 505 A1 | 12/2017 |
| WO | WO 2014/126720 A1 | 8/2014 |
| WO | WO 2018/022590 A1 | 2/2018 |

OTHER PUBLICATIONS

Esther Asensio, "Determination the set-off migration of ink in cardboard-cups used in coffee vending machines" May 14, 2019 (Year: 2019).*

(Continued)

*Primary Examiner* — Maurice C Smith
(74) *Attorney, Agent, or Firm* — Marian E. Fundytus; Ostrolenk Faber LLP.

(57) ABSTRACT

Inks for direct food contact with wide colour gamut and good physical resistance properties, and methods for identifying such inks, for printing such inks, and for packaging foodstuffs with materials printed with such inks.

28 Claims, 8 Drawing Sheets

(51) Int. Cl.
    *C09D 11/322*     (2014.01)
    *C09D 11/36*     (2014.01)
    *C09D 11/40*     (2014.01)

(56) References Cited

U.S. PATENT DOCUMENTS 10,326,914 B2 *   6/2019   Rich ................... C09D 11/322
10,358,559 B2 *   7/2019   Despotopoulou ........ C08K 5/05

OTHER PUBLICATIONS

Wally Ernesto Garcia Castillo, "Folding carton and internal printing: a technical approach to consumer differentiation and food safety", 2017 (Year: 2017).*

International Search Report issued in International Application No. PCT/ES2021/070689, dated May 11, 2022.

Written Opinion of the International Searching Authority issued in International Application No. PCT/ES2021/070689, dated May 11, 2022.

International Preliminary Report on Patentability (Chapter 1 of the Patent Cooperation Treaty) issued in International Application No. PCT/ES2021/070689, dated Dec. 6, 2022.

Euipa: "European Printing Ink Association . EuPIA—a sector of CEPE aisbl EuPIA Guidance on Migration Test Methods for the evaluation of substances in printing inks and varnishes for food contact materials", Aug. 14, 2020, pp. 1-23, XP055885095, Retrieved from the Internet: URL:https://www.eupia.org/fileadmin/FilesAndTradExtx_edm/2020-08-14_EuPIA Guidance_pn Migration_Test Methods.pdf [retrieved on Jan. 28, 2022].

More Simon J et al: "Guidance on the use of the Threshold of Toxicological Concern approach in food safety assessment", The EFSA Journal, vol. 17, No. 6, Jun. 1, 2019, XP055885082, Parma, IT ISSN: 1831-4732, DOI: 10.2903/j.efsa.2019.5708.

* cited by examiner

Coffee capsule - food weight: 5,2 g

Outside Area of the lid:

R= 1,75 cm
A=πr2
A= 9,6 cm2

Lateral side of the capsule --> truncated cone.

R= 1,75 cm
r= 1,2 cm
g= 2,3 cm
A=π(R+r)g (truncated cone)
A= 21,5 cm2

Lower side of the capsule without small lower base -->Truncated cone r = 1,2 cm
r' = 0,45 cm
g' = 0,9 cm
A=π(r+r')g' (truncated cone)
A= 4,7 cm2

Lower base r' = 0,45 cm
A=πr2
A= 0,63 cm2

Total area: 36,5 cm2

SOLVENT-BASED INKS AND COATINGS FOR FOOD CONTACT APPLICATIONS

CROSS REFERENCE TO RELATED APPLICATIONS

The present application is a § 371 National Phase application based on PCT/ES2021/070689 filed Sep. 22, 2021, which claims the benefit of U.S. Provisional Application No. 63/081,440, filed Sep. 22, 2020, the subject matter of each of which is incorporated by reference in their entirety.

The present invention relates to printing inks and coatings suitable for food contact, particularly solvent-based inks comprising organic colourants. As well as being food-safe, the inks and coatings have a wide colour gamut (preferably a gamut value of 400% higher than inks formulated with iron oxide pigments) and have good thixotropic, adhesion and resistance properties. Accordingly, the inks and coatings are suitable in food packaging applications, particularly for direct food contact. The invention further relates to methods of printing substrates with such inks and coatings, methods of packaging utilizing such inks and coatings, methods of identifying such inks, and ink sets comprising a plurality of such inks.

Printed applications have long been used for food and pharma packaging. One specific application is aluminum coffee capsules, which have seen increasing use in recent years. However, the current scenario in this and other applications is that the pigments used are not DFC (Direct Food Contact) pigments.

Direct food contact (DFC) inks are inks which are intended to be in direct physical contact with food, for instance in food packaging or other articles intended to come into contact with food. Thus, DFC inks may be used on the inside of food packaging. For DFC applications, the diffusion path between ink or coating and food is short, and so DFC inks have a greater potential for migration into the food compared to non-direct food contact (non-DFC) inks, which are used on the non-food contact surfaces of food packaging or other articles. The term "non-direct food contact" is also referred to herein as "indirect food contact", and describes a material (such as an ink or coating) which has a functional barrier layer between it and the food substance, wherein there is potential for the material to come into contact with the food substance. An example of an indirect food contact ink is an ink applied to the outside of food packaging or to an intermediate layer of food packaging. Although there is a potential for migration from non-DFC inks, it is lower than the risk with DFC inks.

DFC inks are advantageous in food packaging applications as they reduce the number of layers required in the packaging, thereby increasing sustainability and recyclability. For example, additional laminate layers between the food and ink are not required since the ink can be in direct contact with the food. DFC inks may also be printed directly onto the food product, which means less packaging is required overall.

One of the difficulties with formulating ink and coating compositions suitable for food contact is that the national or regional regulatory frameworks which regulate food contact materials have relatively short lists of allowed and forbidden substances which are suitable for use as food contact inks and coatings. Accordingly, the food packager has a relatively small number of materials from which to choose, and therefore has limited options for the design of images and information to be displayed on the surfaces of food packaging, particularly those surfaces which are in direct contact with the food. Typically, the food packager is limited to inks formulated with iron oxide pigments and/or other inorganic pigments.

It is an object of this invention to provide ink and coating compositions that are suitable for food contact. It is a further object of the invention to provide a method of printing a substrate with an ink or coating composition which is suitable for food contact. It is a further object of this invention to provide a method of packaging a food product wherein a food contact ink or coating composition is present in or on the packaging. It is a further object of the invention to provide an improved methodology to identify inks and coatings that are suitable for food contact. It is a further object of the invention to provide a set of inks or coatings suitable for food contact.

It is an object of the invention that such inks or coatings or sets thereof exhibit a broad colour gamut in order to enable the printing of more vibrant colours and/or more varied designs than is currently possible using the inks and coatings conventional in the art, particularly wherein the colour gamut value is 400% higher than inks formulated with iron oxide pigments. It is a further object of the invention that such inks or coatings, or sets thereof, exhibit good adhesion to the substrate and good physical resistance properties.

The invention is directed to inks and coatings that are suitable for both direct and indirect food contact, and particularly for direct food contact.

The invention is directed to colourants (e.g. pigments) and inks.

SUMMARY OF THE INVENTION

The present invention provides colourants and inks with a large colour gamut, especially for use in DFC applications. As well as having the properties of extended colour gamut, the inks have improved dot printability, and improved physical and chemical resistance properties. This allows brand owners to market packaging containing DFC inks with complex graphics, one example of which is graphics for Nespresso style coffee capsules. The present invention further provides methods of printing or packaging which utilize such colourants and inks, as well as a method for identifying such colourants and inks. The present invention further provides a set of inks comprising a plurality of such inks.

Non-pigmented coatings (overprint varnishes, primers, etc.) are also encompassed by the present invention. Colour gamut is not a concern with the non-pigmented coatings, but it would be advantageous that the coatings be suitable for DFC applications by using raw materials that are safe for such applications.

The present invention provides:

[1] A method of providing or identifying one or more ink or coating composition(s) suitable for food contact, said method comprising the steps of:
 (i) providing one or more colourant(s);
 (ii) identifying the substances and any impurities in said colourant(s), wherein said identification comprises subjecting said colourant(s) to an extraction test;
 (iii) establishing a specific migration limit (SML) for each of the substances identified in step (ii);
 (iv) formulating said one or more colourant(s) into said ink or coating composition, and calculating the proportion of each of the substances identified in step (ii) which is present in a finished printed layer derived from said ink or coating composition;

(v) performing a worst-case calculation by assuming that 100% of each of the substances identified in step (ii) migrates to a foodstuff when contacted with a finished printed layer derived from said ink or coating composition;

(vi) evaluating whether said worst-case calculation in step (v) for each of the substances identified in step (ii) satisfies the criterion of being equal to or greater than the specific migration limit (SML) from step (iii), and if said criterion is satisfied for any of said substances then subjecting said ink or coating composition to migration testing;

(vii) empirically determining by chemical analysis the migration level ($M_L$) of each of said substances identified in step (ii) in one or more migration test(s);

(viii) evaluating whether the migration level ($M_L$) measured empirically in step (vii) for each of said substances in said ink or coating composition satisfies the criterion of being less than the specific migration limit (SML) established for that substance in step (iii), (ix) selecting as an ink or coating composition suitable for food contact those ink or coating composition(s) for which every substance contained therein satisfies the criterion in step (viii);

(x) optionally selecting those ink or coating composition(s) containing one or more substance(s) which fail the criterion in step (viii) to be an ink or coating composition suitable for food contact only in restricted quantities.

[2] A method according to [1] which is a method for identifying a plurality of ink or coating compositions suitable for food contact wherein said plurality of ink or coating compositions constitute a set.

[3] A method according to [1] or [2] wherein said colourant is a commercially available product having one or more impurities declared by the manufacturer thereof.

[4] A method according to any of [1] to [3] wherein said extraction test in identification step (ii) comprises preparing a solution of said colourant and an internal standard in a solvent and analysing the solution, preferably using gas chromatography-mass spectrometry (GC-MS).

[5] A method according to any of [1] to [4] wherein one or more of the specific migration limit(s) in step (iii) is stipulated by regional regulations for food contact, preferably selected from one or more of: the EU Plastics Regulation No. 10/2011; Swiss Ordinance on Materials and Articles 817.023.21 of the Food Safety and Veterinary Office of the Swiss Federal Department of Home Affairs; and US FDA Regulation 178.3297; and Chinese Regulation GB 9685-2008 and its subsequent updates.

[6] A method according to any of [1] to [5] wherein one or more of the specific migration limit(s) in step (iii) is established by a hazard assessment using the Threshold of Toxicological Concern approach developed by the EFSA, or the EFSA and WHO.

[7] A method according to [7] wherein one or more of the specific migration limit(s) in step (iii) is established by a hazard assessment using the Threshold of Toxicological Concern approach developed by the EFSA as set out in EuPIA Guidance for Risk Assessment of Non-Intentionally Added Substances (NIAS) and Non-Evaluated or Non-Listed Substances (NLS) in printing inks for food contact materials (May 2021).

[8] A method according to [6] or [7] wherein the hazard assessment comprises establishing if the substance identified in step (ii) is genotoxic using VEGA QSAR (version 1.1.5) prediction models.

[9] A method according to any of [1] to [8] wherein said specific migration limit(s) in step (iii) is established with reference to the standard EU Cube (10 cm$^3$) exposure model.

[10] A method according to any of [1] to [9] wherein said worst-case calculation in step (v) is performed on the basis of one or more food contact exposure models, preferably selected from the standard EU Cube (10 cm$^3$) exposure model, a yoghurt pot lid exposure model, a cheese packaging cylinder exposure model, and a coffee capsule frusto-conical exposure model.

[11] A method according to any of [1] to [10] wherein said worst-case calculation is performed on the basis of the standard EU Cube (10 cm$^3$) exposure model, optionally wherein one or more additional worst-case calculations are performed using other exposure models by calculating the area of the food contact surface(s) in said other exposure models relative to the area of the food contact surfaces in said EU Cube exposure models, preferably wherein said other exposure models are selected from a yoghurt pot lid exposure model, a cheese packaging cylinder exposure model, and a coffee capsule frusto-conical exposure model.

[12] A method according to any of [1] to [11] wherein said chemical analysis in step (vii) is conducted using gas chromatography-mass spectroscopy (GC-MS) analysis.

[13] A method according to any of [1] to [12] wherein said migration test in step (vii) comprises subjecting the ink or coating composition to one or more, and preferably all, of a food simulant test selected from (a) the 10% ethanol test at 20° C., (b) the 50% ethanol test at 20° C., (c) the hot fill boiled water test and (d) the 3% acetic acid test at 20° C.; and preferably wherein a plurality of migration tests selected from tests (a) to (d) are conducted in which case the migration level ($M_L$) is defined as the highest migration level measured in any of said plurality of migration tests.

[14] A method according to any of [1] to [13] further comprising the following steps subsequent to step (ix) and, where present, subsequent to step (x):

(xi) defining a food contact packaging surface onto which said ink composition(s) are to be disposed and calculating the area $A_{P-MAX}$ of said surface which corresponds to 100% coverage of said surface with said ink or coating composition(s);

(xii) defining an area A% which is the surface area of food contact in the exposure model on the basis of which said specific migration limits (SML) have been established in step (iii);

(xiii) calculating an adjusted migration level ($M_{L-A}$) which is specific to the food contact packaging surface defined in step (xi) wherein $M_{L-A}=M_L \times A_{P-MAX}/A_M$;

(xiv) selecting one or more ink or coating composition(s) suitable for unrestricted use on said food contact packaging surface if the $M_{L-A}$ values of all substances in said composition(s) is less than said SML(s); and (xv) optionally selecting one or more ink or coating composition(s) suitable for restricted use on said food contact packaging surface if the $M_{L-A}$ value of any substance in said composition(s) is equal to or greater than said SML(s), wherein said restricted use is defined by a coverage factor $C_F$, wherein $C_F=(100/M_{L-A})\times 100$, wherein said coverage factor $C_F$ is the maximum fraction of said food contact packaging surface area which can be covered by said one or more ink or coating composition(s) suitable for restricted use.

[15] A method according to any of [1] to [14] wherein said the ink or coating composition further comprises one or more diluents and/or one or more additives additional to said colourant(s), and wherein said method comprises the steps of:
- (i) providing one or more colourant(s), one or more additive(s) and one or more diluent(s);
- (ii) identifying the substances and any impurities in said colourant(s), additive(s) and diluent(s);
- (iii) establishing a specific migration limit (SML) for each of the substances identified in step (ii);
- (iv) formulating said one or more colourant(s) additive(s) and diluent(s) into said ink or coating composition, and calculating the proportion of each of the substances identified in step (ii) which is present in a finished printed layer derived from said ink or coating composition;
- (v) performing a worst-case calculation by assuming that 100% of each of the substances identified in step (ii) migrates to a foodstuff when contacted with a finished printed layer derived from said ink or coating composition;
- (vi) evaluating whether said worst-case calculation in step (v) for each of the substances identified in step (ii) satisfies the criterion of being equal to or greater than the specific migration limit (SML) from step (iii), and if said criterion is satisfied for any of said substances then subjecting said ink or coating composition to migration testing;
- (vii) empirically determining by chemical analysis the migration level ($M_L$) of each of said substances identified in step (ii) in one or more migration test(s);
- (viii) evaluating whether the migration level ($M_L$) measured empirically in step (vii) for each of said substances in said ink or coating composition satisfies the criterion of being less than the specific migration limit (SML) established for that substance in step (iii),
- (ix) selecting as an ink or coating composition suitable for food contact those ink or coating composition(s) for which every substance contained therein satisfies the criterion in step (viii);
- (x) optionally selecting those ink or coating composition(s) containing one or more substance(s) which fail the criterion in step (viii) to be an ink or coating composition suitable for food contact only in restricted quantities or under restricted application conditions.

[16] A method according to [15] wherein said restricted application conditions are selected from a minimum duration of drying and/or a minimum temperature of drying of said ink or coating composition after application to a substrate, particularly wherein the said one or more substance(s) which fail the criterion in step (viii) are selected from diluents and other volatile substances present in said composition.

[17] A method according to any of [1] to [16] wherein said method further comprises the step of evaluating the thixotropy of a concentrate (or pigment base) comprising said colourant in an amount of from about 5 to about 30% by weight, preferably from about 10 to about 30% by weight of the concentrate (or pigment base).

[18] A method according to any of [1] to [17] wherein said method further comprises the step of evaluating the physical or chemical characteristics of a printed layer derived from said ink or coating composition(s) from step (vii), wherein said characteristics are selected from one or more of; adhesion to a substrate; rub resistance; scratch resistance; heat-seal resistance; impact resistance; and solvent resistance.

[19] A method according to any of [1] to [18] wherein said method further comprises the step of evaluating the colour characteristics of a printed layer derived from said ink or coating composition(s) from step (vii), by measuring the L*a*b* colour parameters in the CIELAB (1976) colour space.

[20] A method according to [19] which is a method for identifying a plurality of ink compositions suitable for food contact wherein said plurality of ink compositions constitute an ink set, wherein the method further comprises calculating the colour gamut of the ink set from the L*a*b* colour parameters.

[21] A method according to [20] further comprising selecting ink compositions to provide an ink set which exhibits a gamut value which is at least 400% higher than that of an ink set formulated with iron oxide pigments.

[22] A method according to any of [1] to [21] wherein said one or more ink or coating composition(s) contain a plurality of colourants, preferably comprising two or more and preferably all of yellow, cyan, red and black.

[23] A method according to any of [1] to [22] wherein each of said one or more colourant(s) are organic colourants.

[24] A method according to any of [1] to [23] wherein said one or more ink or coating composition(s) are solvent-based.

[25] A method according to any of [1] to [24] wherein said food contact is direct food contact.

[26] A method of printing a substrate with one or more ink or coating composition(s) suitable for food contact, said method comprising the method defined in any of [1] to [25] and subsequently further comprising printing said one or more ink or coating composition(s) onto a substrate.

[27] A method according to [26] wherein the substrate is an aluminium, paper or polymeric substrate, preferably wherein the polymer is selected from polyethylene terephthalate, polypropylene and polyamide, preferably wherein a polymeric substrate is oriented.

[28] A method according to [26] or [27] wherein said printing is selected from lithographic printing, screen printing, flexographic printing, gravure printing and inkjet printing.

[29] A method of packaging a foodstuff wherein a food contact ink is disposed in or on the packaging, said method comprising the method defined in any of [1] to [28] and further comprising the step of packaging said foodstuff with the printed substrate

[30] A method according to [29] wherein said one or more ink or coating composition(s) are in direct contact with said foodstuff.

[31] A method according to [29] or [30] wherein said packaged foodstuff is a solid or liquid or combination thereof

[32] A method according to any of [29] to [31] wherein, in use, said packaged foodstuff is combined with an additional substance, preferably water, which was not present within said packaging, such that said additional substance is contacted with said packaging, optionally wherein said additional substance is direct contact with a surface on which is disposed said one or more ink or coating composition(s), preferably wherein said packaged foodstuff is a coffee capsule.

[33] An ink or coating composition, or a set of ink or coating compositions, which are suitable for food contact and which are obtained by a method according to any of [1] to [25].

[34] A printed substrate or article which is suitable for food contact and which is obtained by the method of any of [26] to [28].

[35] A packaged foodstuff obtained by the method of any of [29] to [32].

[36] An ink set which is suitable for food contact and which comprises a plurality of ink compositions, wherein the ink set exhibits a gamut value which is at least 400% higher than that of an ink set formulated with iron oxide pigments.

[37] An ink set according to [36] which comprises two or more and preferably all of yellow, cyan, red and black inks.

[38] An ink set according to [36] or [37] wherein each of said one or more colourant(s) are organic colourants.

[39] An ink set according to any of [36] to [38] wherein said one or more ink or coating composition(s) are solvent-based.

BRIEF DESCRIPTION OF THE FIGURES

FIG. 13D also illustrates the method for calculation of the surface area that is exposed.

DETAILED DESCRIPTION OF THE INVENTION

Figure 1:
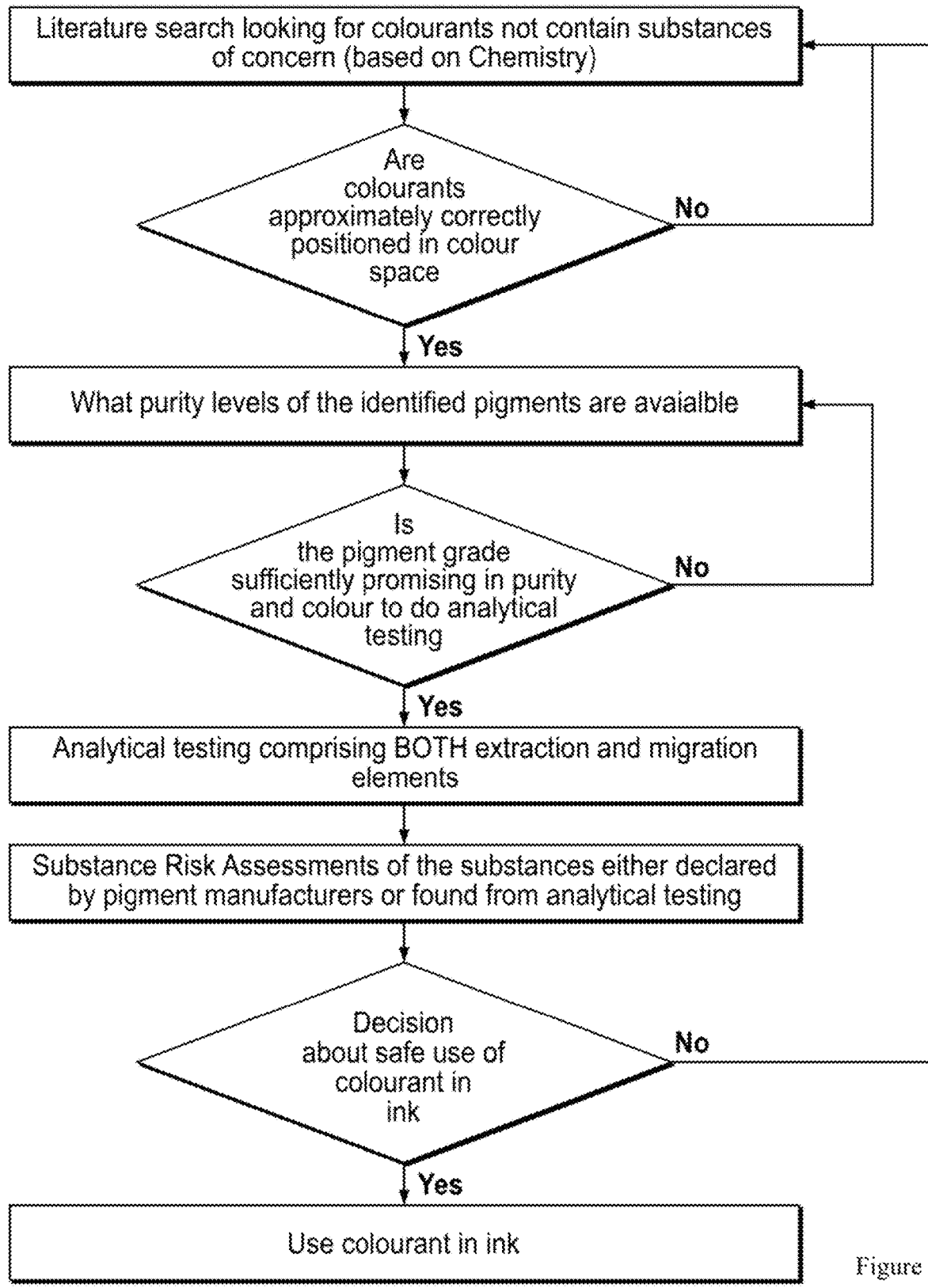
FIG. 1 is a flow chart illustrating the detailed process for identifying organic colourants encompassed by the present invention.

A typical multilayer printed structure has the following layer structure: Overprint varnish/Coloured ink/White ink/Primer/Substrate, in that order.

The colourants used in the present invention are preferably pigments, rather than dyes. The choice of colourants is a key aspect to the present invention. The colourants used in the present invention are preferably organic colourants. A plurality of colourants according to the present invention constitute a DFC ink set.

There are three main regulatory frameworks in the world which regulate food contact materials (FCMs), these being USA, Europe and China. Within these three frameworks there is no existing list of organic pigments which are suitable for direct food contact (DFC) ink applications.

The US FDA has FDA178.3297 that regulates colourants for polymers, but this list is quite old and therefore it does not properly consider non-intentionally added substances (NIASs) that are an inevitable part of the colourant. It lists mainly inorganic pigments, and it results in a very limited colour gamut. As will be understood in the art, NIASs include impurities in materials used in a food packaging ink; a decomposition or reaction product formed during the production of a food packaging ink; or a decomposition or reaction product formed during the life-cycle of the printed food packaging.

The European regulations have a list of approved food colourants and there are a number of existing direct food contact inks that utilize these food colourants. However, as shown by a recent European Food Safety Agency (EFSA) study (September 2016), being a food colourant is not sufficient to guarantee safety in use in DFC printing inks. In addition, the use of these food colourants in DFC inks leads to a limited colour gamut, and in most cases to reduced resistance properties including both lightfastness and chemical resistance.

Some colourants are approved for use in cosmetic applications, and on first inspection it might appear that these could be good candidates for DFC ink colourants. However, on closer inspection, the regulatory purity constraints on colourants for cosmetics is often less severe than that for inks for food packaging. An example of this is the Council of Europe AP(89)1 standard, which applies to the use of colourants in plastic materials and articles coming into contact with food and which is adopted by most ink manufacturers and by some regulatory authorities, and has a restriction for PAA content (primary aromatic amine) in the colourant. The European Cosmetics Regulation does not have such a restriction.

All three of the main food contact material (FCM) regulatory systems (i.e. US. Europe and China) are aimed at preventing substances from migrating into food at levels which could endanger human health. There is some variation in how this is phrased, with for example, the FDA regulations referring to unintentional food additives, but the intention is the same.

In the present invention, the inventors used their knowledge of pigment chemistry along with their analytical capability and regulatory risk assessment skills to identify colourants which can be used in DFC inks and which do not contain substances that will migrate into food at levels which could endanger human health or become unintentional food additives at levels which could endanger human health.

An example of a general process according to the invention to identify colourants, preferably organic colourants, and other materials suitable for direct food contact (DFC) inks is illustrated in the flowchart shown in FIG. 1 and is described in more detail below:

(1) Initially, the inventors considered which pigment colour index numbers would be likely to not contain substances that were of concern. This step may involve conducting a literature search for colourants (preferably organic colourants, preferably organic pigments) that do not contain substances of concern based on their chemistry. Substances of concern are those that migrate at toxic levels, i.e. at concentrations that could endanger human health. Substances that are known to migrate at toxic levels include primary aromatic amines typically used in azo (red, orange, yellow) pigments and hexachlorobenzene in phthalocyanine green pigment. For most of the intentionally used substances in pigments there are documented safe levels of exposure in recognised documents such as the EU Plastics Regulation No. 10/2011; Swiss Ordinance on Materials and Articles 817.023.21 of the Food Safety and Veterinary Office of the Swiss Federal Department of Home Affairs; and US FDA Regulation 178.3297; and Chinese Regulation GB 9685-2008 and its subsequent updates.

(2) After identifying such colourants, a determination was made whether the colourants were correctly or suitably positioned in colour space to provide a wide colour gamut. Thus, the inventors considered the position of the pigments in the colour space, so that they provide a wide colour gamut in the final product. If the colourants are not correctly or suitably positioned in the colour space, then a further literature search for colourants is conducted according to step (1) which are then assessed for their position in colour space according to step (2).

(3) After identifying suitable colourants in step (2), specific grades of pigment (of the colour index numbers identified in step 1) which would not contain substances that migrate at toxic levels were identified. That is, the inventors determined the purity levels of the pigment grades containing the colour index numbers identified in step (1), thereby allowing an assessment of whether or not a given pigment grade was sufficiently promising in purity and colour to proceed to the next stage of analytic testing. If the pigment grade is not sufficiently promising in purity and colour then alternative pigment grades are sought.

(4) The other components of the ink/coating composition, i.e. raw materials such as resins, solvents, additives, etc., are then selected from those which are food safe and/or have low migration levels. Once the other ink/coating materials have been selected they are combined with the pigment grade selected according to step (3) in order to formulate an ink or coating composition.

(5) The pigments from step (3) were subjected to an extraction test. Suitable extraction tests are described below. As will be understood in the art, extraction testing can be performed by any suitable analytical technique such as gas chromatography mass spectrometry (GC-MS).

(6) The inventors used the information about the known impurities within the pigments from the pigment manufacturers along with the analytical data from the extraction testing to establish what substances in the colourants could have some regulatory concern. The inventors then performed a substance risk assessment of the substances either declared by the pigment manufactures or found from analytic testing. To perform the substance risk assessment, the inventors first established a Specific Migration Limit (SML) for each of these substances. Some of the substances have published Specific (or Safe) Migration Limits, but many do not because NIAS's are out of scope of many of the specific regulations. However, it is still possible to use a risk assessment-based methodology, considering the toxicology of the substance and an appropriate exposure model to create a self-derived specific migration limit. The self-derived migration limits (or levels) may be derived from a hazard assessment following the process set out in the EuPIA (European Printing Ink Trade Association) document: EuPIA Guidance for Risk Assessment of Non-intentionally Added Substances (NIAS) and Non-Evaluated or Non-Listed Substances (NLS) in printing inks for food contact materials. This document follows EFSA (European Food Safety Authority) methodology. In the present invention, the self-derived specific migration limits are derived on the basis of the standard EU Cube exposure model. The specific migration limits (including the self-derived specific migration limits) are compared with the worst-case calculations. The worst-case calculation is based on 100% migration from the dried film to the food and is based on the standard EU Cube exposure model, the yoghurt pot lid exposure model, cheese packaging exposure scenario or coffee capsule exposure mode which are described below.

(7) Migration testing is then conducted, which suitably involves printing the ink composition (e.g. from step (4)) onto a substrate (e.g. an aluminium foil; for instance at a coat weight of 2.0 $g/m^2$) and empirically determining by chemical analysis the migration level of each of the identified substances. Suitable migration tests are described below.

The inventors are able to make a decision about safe use of the colourant in the ink. If the colourant is determined to be not safe for use in the ink then the process is repeated. If the colourant is determined to be safe, then it is used in ink, preferably a DFC ink.

Using this methodology, the inventors were advantageously able to show that the materials used do not contain substances that will migrate into food at levels which could endanger human health, with a significant margin for safety.

In the present invention, an extraction test preferably involves preparing a solution of the pigment and an appropriate internal standard or calibrant (i.e. a known compound which is added to a sample in a known amount to determine the quantity of the unknown compound(s) in an analytical technique; also referred to as a reference standard), such as tributyl phosphate, in a suitable solvent. Suitable solvents include ethanol (preferably absolute ethanol) and dichloromethane. The solution is then analysed using any suitable analytical technique, preferably gas chromatography-mass spectrometry (GC-MS).

As will be understood in the art, the amount of substance that will migrate into a food is dependent on the chemistry of the food as well as contact times and temperatures. Accordingly, in the present invention, migration testing is preferably performed using one or more food simulants selected from 10% ethanol at 20° C.; 50% ethanol at 20° C.; 100% water at 100° C.; and the 3% acetic acid test at 20° C.

In a preferred embodiment, the inventive ink set comprises, as a minimum, the following individual inks:
DFC Black
DFC Red
DFC Yellow
DFC Cyan
DFC Clear (non-pigmented version of the coloured inks, generally a blend of Example 2A) DFC Technical Varnish (with wax and/or additives as needed)

In a preferred embodiment the inks are made from a blend formulation of two intermediates (i.e. a pigment concentrate and a technology varnish), in which case, the pigment concentrate would provide the correct shade and colour strength, while the technology varnish provides the chemical and physical resistance properties.

It is also possible to produce the inks without first making a pigment concentrate and varnish by simply grinding the pigment into a base and blending the resultant material with the remaining ink formulation ingredients.

In a preferred embodiment, a primer and overprint varnish (OPV) if necessary, is added to the print construct to enhance resistance properties of the final structure.

The inks may also be used with or without an OPV, and preferably still retain their overall resistance properties.

Examples of the types of materials that would be typically used in the inks of the present invention include (but are not limited to) those discussed below.

Preferably, the inks or coating of the present invention comprise one or more pigment(s) (typically, the pigments are not dyes).

The inks and coatings of the present invention may also include one or more of the following resins: vinyl, polyurethane, polyurea, polyurethane urea, polyester, polyisocyanate, polyvinylidene chloride (PVDC), cellulosic resins (e.g. cellulose acetate butyrate (CAB) or cellulose acetate propionate (CAP)), acrylic, ketonic resins, maleic resins. The resins are food safe and/or have low migration levels and are therefore suitable for use in direct food contact inks.

Preferably, one or more resins is a polyurethane urea. More preferably, one or more resins is a polyurethane urea derived from a polyurethane pre-polymer being the reaction product of; a diisocyanate component; and, a diol component having (i) a first diol having a molecular weight below 2000; and (ii) a polymeric diol having a molecular weight below 3000; wherein the —NCO/—OH ratio is less than 2; the polyurethane pre-polymer contains 1.3 to 6.0 wt. % of unreacted —NCO groups; and 80 to 120% of a diamine, based on the equivalents of the unreacted —NCO groups; and whereby the resulting poly(urethane/urea) resin is soluble in organic solvent.

Unless otherwise stated, a reference to "molecular weight" or "average molecular weight" is preferably to the weight average molecular weight ($M_w$). The molecular weight can be measured by those techniques known in the art such as gel permeation chromatography. For instance, molecular weight determination may be conducted on a Hewlett-Packard 1050 series HPLC system equipped with two GPC Ultra styragel columns, 103 and 104 Å (5 μm mixed, 300 mm×19 mm, Water Millipore Corporation, Milford, MA, USA) and THF as mobile phase. Preferably, molecular weight is calculated by comparison with a polystyrene standard.

Many different solvents can be considered in this application, such as esters (ethyl acetate and propyl acetate), ketones (methyl ethyl ketone and acetone), alcohol (ethanol, n-propanol and isopropanol), glycol (ethoxy propanol and methoxy propanol), and water.

As with most ink and coating compositions, additives may be incorporated to enhance various properties. A partial list of such additives includes but is not limited to adhesion promoters, silicones, light stabilizers, flow promoters, defoamers, antioxidants, stabilizers, surfactants, dispersants, plasticizers (monomeric such as acetyl tributyl citrate (ATBC) and dibutyl sebacate (DBS) or polymeric such as polyvinyl butyral (PVB)), rheological additives, waxes, silicones, etc.

The printing ink may also include waxes such as but not limited to amide wax, erucamide wax, polypropylene wax, paraffin wax, polyethylene wax, Teflon®, carnauba wax and the like. The wax may be a combination of said waxes.

The inventive inks are preferably suitable for printing on aluminum, PET (polyethylene teraphthalate), coated PET, metallized PET, OPP (oriented polypropylene), metalized OPP, OPA (oriented polyamide) or paper, but not limited to these.

There is no restriction on the type of inks that could be formulated according to the present method. Inks for lithographic, screen, flexo, gravure, inkjet, etc. would all be within the scope of the present invention.

Figure 2:
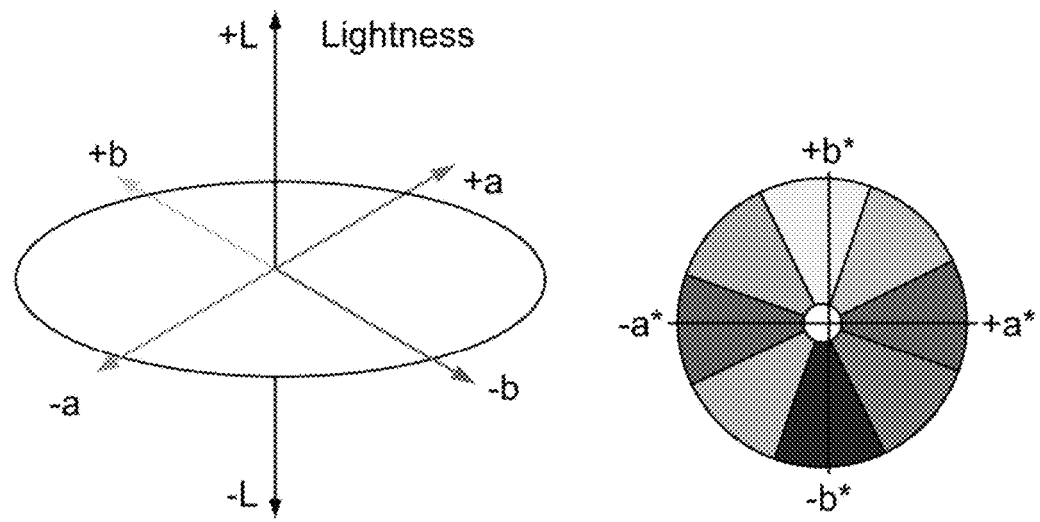
FIG. 2 illustrates the CIE Lab colour space system. Specifically, the left-hand image shows the CIE L*a*b* colour sphere and the right-hand image shows the colour circle obtained by taking a horizontal slice through the colour sphere.

Regarding colour properties of the inks, and in order to describe the colour in a numerical way, the CIE (International Commission of Illumination) defined the CIELab (1976) system (FIG. 2). In CIE L*a*b* colour space, colours are arranged in a "sphere". The lightness/darkness of the colour is described by a vertical axis running though the center, from black at 0 to white at 100. The lighter the colour, the higher the lightness value. If we take a horizontal slice though the "sphere", we get a circle of colour.

The redness/greenness of a colour is expressed by the value of the "a" axis, running from right to left: +(positive) "a" indicates a red, – (negative) "a" indicates a green.

The blueness/yellowness of a colour is expressed by the value of the "b" axis, running from top to the bottom: +(positive) "b" indicates a yellower colour, – (negative) "b" indicates a bluer colour.

According to the CIE, colour gamut could be described as volume, area or solid in a colour space, consisting of all those colours that are either:
(a) present in a specific scene, artwork, photograph, or photomechanical or other reproduction; or
(b) capable of being created using a particular output device and/or media.

As used herein, colour gamut is defined as the range of colours which a particular device can produce or record. One very important aspect of colour gamuts is that they are three dimensional, not two dimensional. In particular, gamut is a three-dimensional measurement of colour, measuring the lightness (L*), redness/greenness (a*), and blueness/yellowness (b*). When we describe a colour, it usually consists of three components.

Colour gamut of the inks described herein is the range of colours which the inks exhibit.

Having established the L*a*b* parameters of an ink, it is possible to calculate the volume of the colour space contained in the gamut. The volume is calculated as a sum of all the volumes of the cubes (each cube is 1 unit of L*a*b*) filling the gamut space.

Unless stated otherwise, gamut is measured herein using an X-Rite Exact spectrophotometer (illuminant D50; observer angle 2°) which a number which represents the volume (using L*a*b* cubes) in which all the possible colours that can be made are enclosed. The higher the number, the bigger the amount of colours that can be created.

The invention is further described by the following numbered paragraphs:
1. A set of solvent-based DFC printing inks comprising organic colourants, and wherein all of the materials contained within the ink formulations meet the safety migration limits and show a GAMUT value of 400% higher than inks formulated with iron oxide pigments.
2. The ink set of paragraph 1, wherein the migration limits for all materials are below the threshold for a human of 60 kg in accordance with the EU Cube Model.
3. The ink set of paragraph 1, wherein the ink set comprises yellow, cyan, red and black.
4. A process for formulating a DFC ink set, comprising:
    a. establishing a safe migration limit for each material used in the inks system; and
    b. using only those materials that meet the safe migration limit.
5. A process for identifying organic colourants for a DFC ink set, comprising
    a. establishing a safe migration limit for each colourant; and
    b. selecting those colourants that show a GAMUT value of 400% higher than inks formulated with iron oxide pigments.
6. A printed article comprising the printing ink set of paragraph 1-3
7. The article of paragraph 6 being suitable for DFC applications.
8. The article of paragraph 7 being a food packaging article.
9. The article of paragraph 8, meeting the application 1, 2 and 3 exposure scenarios described in the Example section below.

The present invention has been described in detail, including the preferred embodiments thereof. However, it will be appreciated that those skilled in the art, upon consideration of the present disclosure, may make modifications and/or improvements on this invention that fall within the scope and spirit of the invention.

Examples

The following examples illustrate specific aspects of the present invention and are not intended to limit the scope thereof in any respect and should not be so construed.

PU-1171 is a solvent-soluble poly(urethane/urea) resin derived from a polyurethane pre-polymer being the reaction product of: a diisocyanate component; and a diol component having (i) a first diol having a molecular weight below 2000; and (ii) a polymeric diol having a molecular weight below 3000; wherein the —NCO/—OH ratio is less than 2; the polyurethane pre-polymer contains 1.3 to 6.0 wt. % of unreacted —NCO groups; and 80 to 120% of a diamine, based on the equivalents of the unreacted —NCO groups; whereby the resulting poly(urethane/urea) resin is soluble in organic solvent.

TABLE 2

Example 2A Technology Varnish (TV) coded as SA1288

| Raw materials | wt % |
| --- | --- |
| PU-1171 poly urethane urea resin | 55 |
| MOWITAL B 16H | 2.1 |
| CAB 381-0.5 | 4 |
| CERETAN MX 9820 | 2.5 |
| ETHANOL | 10.4 |
| ETHYL ACETATE | 26 |
| Total | 100 |

TABLE 3

Example 3A Technology Varnish coded as SA1385

| Raw materials | wt % |
| --- | --- |
| PL-1171 poly urethane urea resin | 40.5 |
| MOWITAL B 16H | 2.1 |
| CAB 381-0.5 | 4 |
| CERETAN MX 9820 | 2.5 |
| Aerosil 200 | 2.5 |
| Nitrocellulose Varnish grade 30A | 12 |
| ETHANOL | 10.4 |
| ETHYL ACETATE | 26 |
| Total | 100 |

TABLE 1

Example 1A-1D pigment concentrates (bases):

| Raw materials (wt %) | Ex 1A Yellow base SA1183 | Ex 1B Red base SA1166 | Ex 1C Cyan base SA1178 | Ex 1D Black base SA1471 |
| --- | --- | --- | --- | --- |
| PALIOTOL YELLOW D 1819 | 19 | | | |
| IRGAZIN RUBINE L 4025 | | 18 | | |
| HELIOGEN BLUE D6840 | | | 18 | |
| C472222. SunCroma D&C BLK 2 | | | | 20 |
| PU-1171 poly urethane urea resin | 14 | 20 | 20 | 16.4 |
| MOWITAL B 16H | 2.7 | 2.7 | 2.31 | 2.7 |
| ETHANOL | 23.3 | 24.3 | 20.39 | 21.9 |
| NORMAL PROPANOL | 14 | 10 | 10.7 | 10 |
| TAP WATER | 2 | 2 | | 2 |
| ETHYL ACETATE | 25 | 23 | 28.6 | 27 |
| Total | 100 | 100 | 100 | 100 |

TABLE 4

Example 4A-4D Finished Inks:

| inks (wt %) | Ex. 4A Yellow ink SBDEV977 | Ex. 4B Red ink SBDEV980 | Ex. 4C Cyan ink SBDEV976 | Ex. 4D Black ink SBDEV979 |
|---|---|---|---|---|
| Ex. 1A Yellow Base | 45 | | | |
| Ex. 1B Red Base | | 45 | | |
| Ex. 1C Cyan Base | | | 45 | |
| Ex. 1D Black Base | | | | 45 |
| Ex. 2A TV | 40 | 40 | 40 | 40 |
| ETHANOL | 10 | 10 | 10 | 10 |
| ETHYL ACETATE | 5 | 5 | 5 | 5 |
| Total | 100 | 100 | 100 | 100 |

TABLE 5

Example 5A-5D Finished Inks:

| Inks (wt %) | Ex. 5A Yellow ink SBDEV1287 | Ex. 5B Red ink SBDEV1285 | Ex. 5C Cyan ink SBDEV1286 | Ex. 5D Black ink SBDEV1284 |
|---|---|---|---|---|
| Ex. 1A Yellow Base | 45 | | | |
| Ex. 1B Red Base | | 45 | | |
| Ex. 1C Cyan Base | | | 45 | |
| Ex. 1D Black Base | | | | 45 |
| Ex. 3A TV | 40 | 40 | 40 | 40 |
| ETHANOL | 10 | 10 | 10 | 10 |
| ETHYL ACETATE | 5 | 5 | 5 | 5 |
| Total | 100 | 100 | 100 | 100 |

The inventive ink set also includes, the following Extender Varnishes (EV) that are non-colourant versions of the finished inks. The varnishes could be used either as overprint varnishes (OPVs) or as "letdown" varnishes (i.e. added to the finished inks to lower the colourant concentration for specific customer colour requirements).

TABLE 6

Extender varnish (SBDEV978: TEST DFC S1 EXTENDER VSH) for the 4A-4D inks:

| Raw materials | wt % |
|---|---|
| PU-1171 poly urethane urea resin | 33 |
| MOWITAL B 16H | 1.8 |
| CAB 381-0.5 | 1.6 |
| CERETAN MX 9820 | 1.0 |
| ETHANOL | 26.6 |
| ETHYL ACETATE | 36 |
| Total | 100 |

TABLE 7

Extender varnish (BDEV1294: TEST DFC S2 EXTENDER VSH) for the 5A-5D inks:

| Raw materials | wt % |
|---|---|
| PU-1171 poly urethane urea resin | 24.3 |
| MOWITAL B 16H | 1.8 |
| CAB 351-0.5 | 1.6 |
| CERETAN MX 9820 | 1.0 |
| Aerosil 200 | 1 |
| Nitrocellulose Varnish grade 30A | 7.7 |
| ETHANOL | 26.6 |
| ETHYL ACETATE | 36 |
| Total | 100 |

Ink Evaluation of Colour and Other Properties

First, a preliminary evaluation of the thixotropy of the pigment bases was performed.

Test 1: Evaluation of Pigment Base Thixotropy

Thixotropy is defined as the progressive decrease in viscosity with time for a constant applied shear stress, followed by a gradual recovery when the stress is removed. (See, for example. Science Direct, The Interstitial Environment, A. McLachlan. A. C. Brown, in The Ecology of Sandy Shores (Second Edition), 2006.) Thixotropy refers to the recovery of structure following shear. The speed of structural recovery and the thoroughness define a material's thixotropic behavior. Viscosity (specifically, thixotropy) is measured prior to, during, and after shear to characterize recovery after shear.

In this test the thixotropy of the pigment bases was evaluated at a temperature of 25° C. using a flat-plate geometry, checking the viscosity values with different shear rates. In that way it is possible to determine the real thixotropy of the base near stillness, with no movement. To assess the thixotropy of the pigment bases, Discovery Series Hybrid Rheometer (DHR) HR-1 from TA Instruments is used, in a method comprising three steps:

Step 1: High shear rate (2000 $s^{-1}$), for 20 seconds. In this step the viscosity of the base is low, it flows easily.

Step 2: Low shear rate (10 $s^{-1}$, i.e. close to no movement) for 300 seconds. In this low-shear rate step the base is nearly still, with no movement, therefore it shows the base's difficulty to flow with no shear rate (base capability to flow in a dosing station without stirring device). In general, the viscosity increases in this second step. The higher the viscosity in this step, the higher the thixotropy of the base.

Step 3: Return to high shear rate (2000 $s^{-1}$), for 20 seconds. After the viscosity increase of the previous step, the viscosity decreases again at 2000 $s^{-1}$.

Results are graded on a 1-5 basis with 1 being very high thixotropy, and 5 being very low thixotropy. A grade of 3-5 is considered a pass. In order to assign a 1-5 value, it is necessary to determine the viscosity ranges, which are assigned as follows:

1=Viscosity of Step 2 is higher than 50 Poise;
2=Viscosity of Step 2 is 30-50 Poise;
3=Viscosity of Step 2 is 20-30 Poise;
4=Viscosity of Step 2 is 10-20 Poise;
5=Viscosity of Step 2 is 0-10 Poise.

Printing

Figure 3:
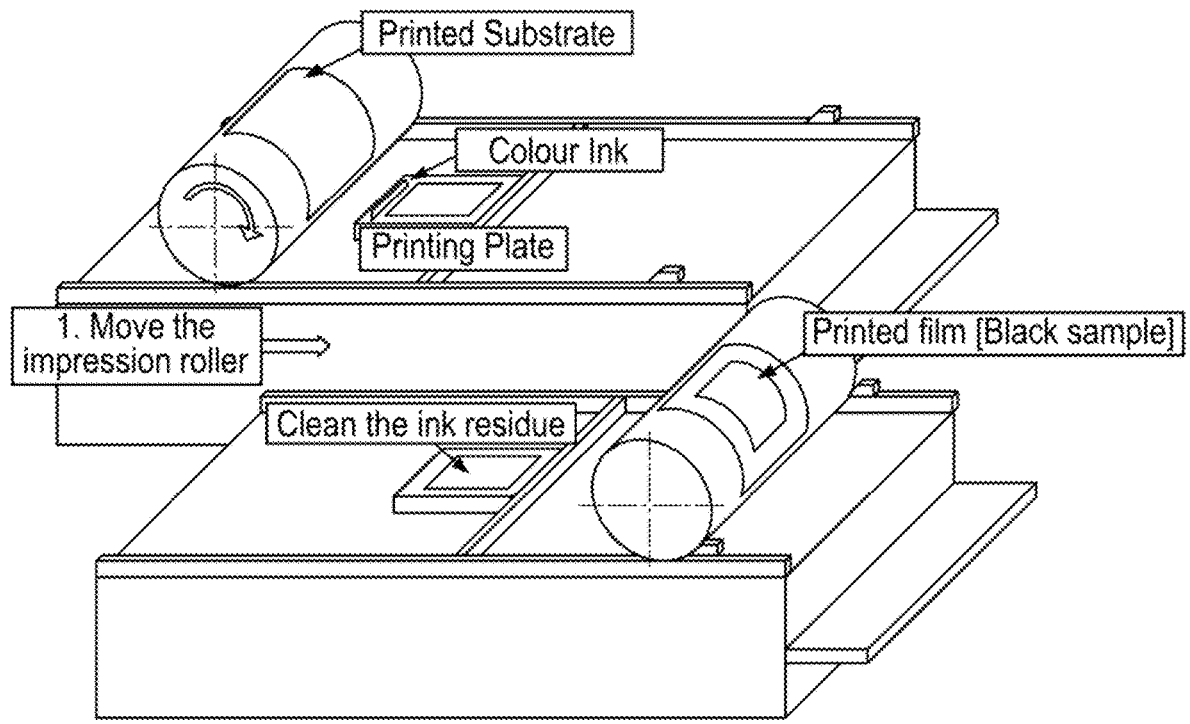
FIG. 3 illustrates a gravure printing machine (Soldan) and the process for printing using a gravure printing machine.

The viscosity of each of the finished ink compositions described hereinabove was reduced to 14-16 seconds using Ford 4 Cup, at 22° C. and printed on a substrate (e.g. aluminium foil) using a gravure printing machine (Soldan) using different plates, as in FIG. 3, to a dry coating weight of 2.0±0.2 g/m². In this type of machine, the substrate is placed on the roller and the inks are placed on the printing plate. Subsequently, the roller is moved, and the substrate is printed with the corresponding inks. Finally, the ink film is dried thoroughly with a hair drier and the ink residue is cleaned from the printing plate. The printed substrate is used for TESTS 2 to 6 below.

The dry coating weight of the ink may be varied to the desired value by an appropriate combination/selection of the plates, as the skilled person is aware. Examples of suitable printing plates for use in the present invention are shown in Table 8.

| Plates and the corresponding characterstic of the cells. | | | |
|---|---|---|---|
| Plate | Volume (cm³/m²) | Cell opening [μm] | Cell depth [μm] |
| 70/0 | 17 | 180 | 50 |
| 70/2 | 10 | 130 | 40 |
| 70/3 | 20 | 190 | 55 |
| 70/4 | 12 | 120 | 35 |

Test 2: Adhesion

Adhesion was tested after printing using adhesive tape TESA 4101PV2. The tape is adhered firmly to the printed surface and smoothed down, leaving a free end. The free end of the tape is then pulled back at an angle of approximately 90° with the tape being removed quickly with a steady pull. The print is then checked visually for ink removal. Results are graded qualitatively on a 1-5 basis with 1-2 being poor (extensive ink removal); 3 being a marginal failure (moderate ink removal); and 4-5 being good-excellent (slight or no ink removal). A grade of 4 or 5 is considered a pass.

Test 3: Rub Resistance

Using a Sutherland Rub Tester at 7 psi (room temperature), the felt pads are placed over the printed side of the substrate and the print area is rubbed for 300 cycles. Once the cycles have finished, the print is checked visually for ink removal. Results are graded qualitatively on a 1-5 basis with 1-2 being poor (extensive ink removal); 3 being a marginal failure (moderate ink removal); and 4-5 being good-excellent (slight or no ink removal). A grade of 4 or 5 is considered a pass.

Test 4: Scratch Resistance

The print is laid on a hard surface. The back of the nail of the index finger is scratched vigorously across the printed surface. The print is then checked visually for ink removal. Results are graded qualitatively on a 1-5 basis with 1-2 being poor (extensive ink removal); 3 being a marginal failure (moderate ink removal); and 4-5 being good-excellent (slight or no ink removal). A grade of 4 or 5 is considered a pass.

Test 5: Heat Seal Resistance

Figure 4:
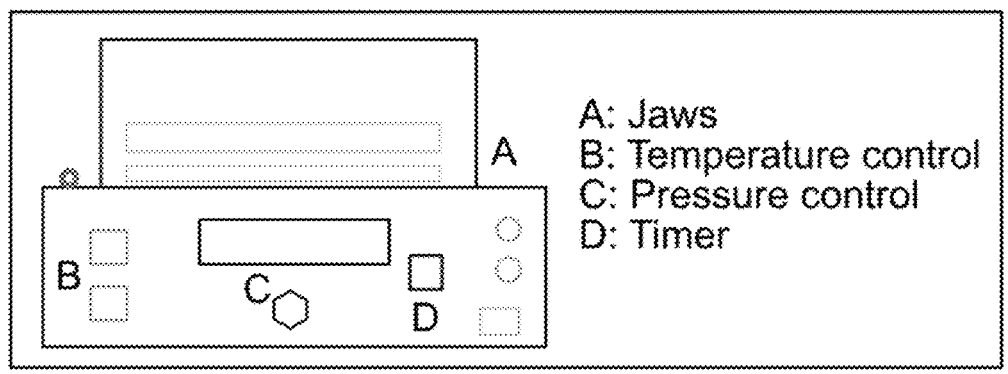
FIG. 4 illustrates a typical heat sealer machine that can be used to measure heat seal resistance of a printed substrate. As shown there, a typical heat sealer includes jaws (A), a temperature control (B), a pressure control (C) and a timer (D).

Pressure is set at 1 bar for 1 second, and heat-sealing is tested at 200° C. using a heat sealing machine (shown schematically in FIG. 4). A print is placed against non-treated side of an aluminium foil, pressure is applied, the print is allowed to cool and the aluminium foil is peeled away from the print surface. The print and the aluminium foil are inspected for ink removal. Results are graded qualitatively on a 1-5 basis with 1-2 being poor (extensive ink removal); 3 being a marginal failure (moderate ink removal); and 4-5 being good-excellent (slight or no ink removal). A grade of 4 or 5 is considered a pass.

Test 6: Impact Test

Figure 5:
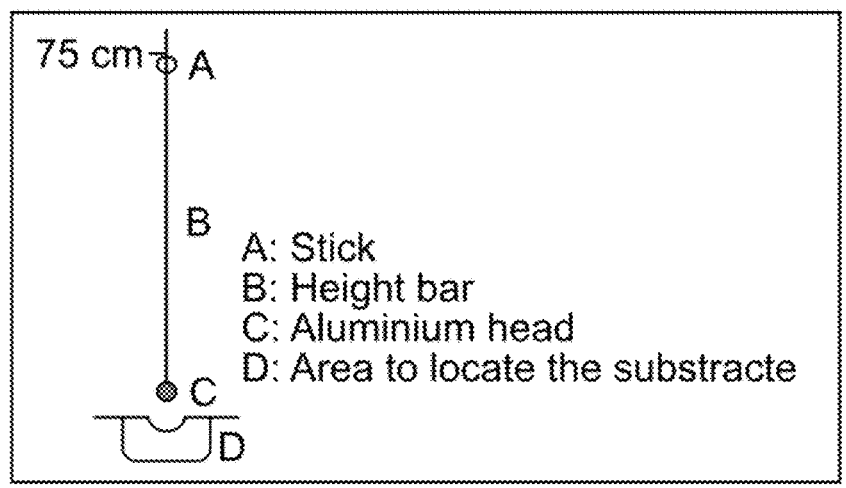
FIG. 5 illustrates typical equipment that can be used to measure the impact test of a printed substrate. As shown therein, typical equipment for impact test measurement includes a stick (A), a height bar (B), an aluminium head (C) and an area (D) to locate the printed substrate that is being measured.

The impact test equipment used is shown schematically in FIG. 5. The test can be done using different drop heights (75 cm is the most aggressive one). The print is placed in the bottom of the equipment, in "area D", with the printed side of the substrate face down, just below the aluminium head (C) which is going to make the mark. The stick (A) is set to a desired height and allowed to drop. The stick impacts with the aluminium head (C) (diameter of 20 mm and weight of 33 g), which makes a mark in the substrate. The printed side of the substrate is visually checked for ink cracking/ink film failure. There are two variables in this test. One is the diameter of the aluminium head, and the other one is the height. Results are graded on a 1-5 basis with 1 being poor and 5 being excellent, and wherein a grade of 3-5 is considered a pass:

1=Severe film failure (film failure area is >50% of the tested area);
2=Moderate film failure (film failure area is 40 to 50% of the tested area);
3=Slight film failure (film failure area is 25 to less than 40% of the tested area);
4=Very slight film failure (film failure area is 10 to less than 25% of the tested area);
5=Minimal film failure (film failure area<10%).

Test 7: Heated Solvent (Ethanol) Resistance

Printed and shaped capsules are placed in solvent under the following conditions:

Solvent: 20% ethanol in water.
Temp: 70° C.
Duration: 2 hours.

Test 8: Extreme Heated Solvent (Ethanol) Resistance

Figure 6:
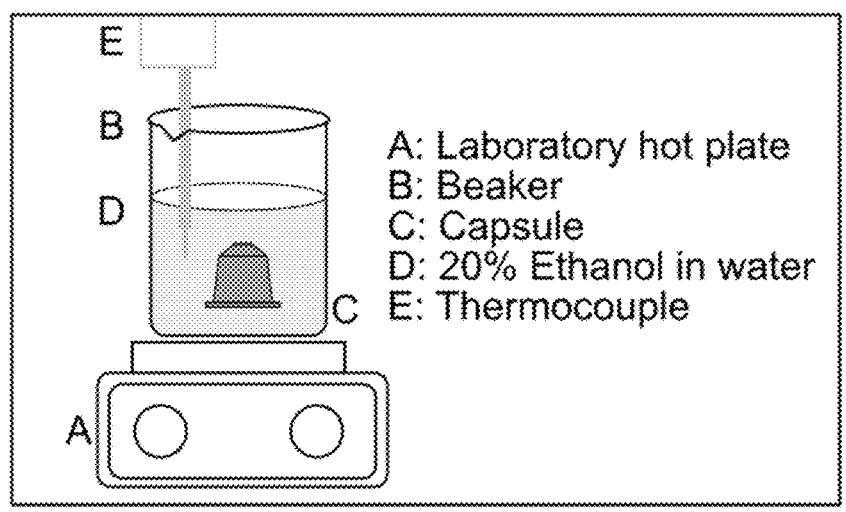
FIG. 6 illustrates a typical assembly that can be used to measure (extreme) heated solvent resistance of a printed substrate. As shown therein, a typical assembly for measuring (extreme) heated solvent resistance includes a laboratory hot plate (A), a beaker (B), the substrate (a capsule in this figure; C), the solvent (20% ethanol in water in this figure; D) and a thermocouple (E).

In a stricter (higher temperature) version of TEST 7, printed and shaped capsules are placed in solvent under the following conditions:

Solvent: 20% ethanol in water
Temp: 87° C. (boiling temperature)
Duration: 1 hour A suitable assembly for TEST 7 & TEST 8 is shown schematically in FIG. 6. In TEST 7 & TEST 8, solvent resistance tests are performed using the following steps:

I. The solvent mix is prepared and heated to the proper temperature.
II. Once the desired temperature is achieved, capsules are submerged in the solvent mix.
III. Capsules remain submerged for the prescribed time.
IV. After the time elapses, the capsules are removed from the beaker.
V. Capsules are allowed to dry at room temperature.

The capsule is visually checked for ink peeling/delamination. Results are graded on a 1-basis with 1 being poor and 5 being excellent, and wherein a grade of 3-5 is considered a pass:
1=Severe ink delamination (delaminated area is >50% of the capsule area);
2=Moderate ink delamination (delaminated area is 40 to 50% of the capsule area);
3=Slight ink delamination (delaminated area is 25 to less than 40% of the capsule area);
4=Very slight ink delamination (delaminated area is 10 to less than 25% of the capsule area);
5=Minimal ink delamination (delaminated area<10%).

Results from TESTS 1 to 8

Table 9 presents the results from TESTS 1 to 8 and demonstrates that the inks of the present invention have the required performance properties needed in various food packaging applications.

TABLE 9

Performance Properties for 4A-4D inks in TESTS 1 to 8:

| Test | Ex. 1A Yellow base SA1183 | Ex. 1B Red base SA1166 | Ex. 1C Cyan base SA1178 | Ex. 1D Black base SA1471 |
|---|---|---|---|---|
| 1. Thixotropy | 5 | 3-4 | 3-4 | 3 |

| Inks/Test | Ex. 4A Yellow SBDEV977 | Ex. 4B Red SBDEV980 | Ex. 4C Cyan SBDEV976 | Ex. 4D Black SBDEV979 |
|---|---|---|---|---|
| 2. Adhesion | 4 | 5 | 5 | 4 |
| 3. Rub Resistance | 5 | 5 | 5 | 4 |
| 4. Scratch Resistance | 5 | 5 | 5 | 4 |
| 5. Heat Seal Resistance | 5 | 5 | 5 | 5 |
| 6. Impact Test | 4 | 4 | 4 | 3 |
| 7. Heated Solvent resistance (70° C.) | 4 | 3 | 3 | 3 |
| 8. Heated Solvent resistance (boiling) | 4 | 3 | 3 | 3 |

All properties are graded on a 1-5 scale, with 1 being worst and 5 being best

Test 9: Colour Evaluation

Print preparation: the viscosity of each of the finished ink compositions described hereinabove was reduced to 14-16 seconds in Ford Cup 4 at a temperature of 22° C. and printed on PET corona-treated film, using a Gravure printing machine (FIG. 3), to a dry coating weight of 2.0±0.2 g/m². The reverse side of the printed PET is placed on the white area of a standard Leneta Form 2A opacity chart for colour measurement, and the L*a*b* colour parameters of prints of the inventive inks were measured using an X-Rite Exact spectrophotometer (illuminant D50; observer angle 2°). The results are shown in Table 10.

TABLE 10

Colour property measurements of inventive inks in TEST 9

| inks/colour parameters | L* | a* | b* |
|---|---|---|---|
| Ex. 4D Black ink SBDEV979 | 2.09 | 0.05 | −0.49 |
| Ex. 4B Red ink SBDEV980 | 39.48 | 74.01 | 44.4 |
| Ex. 4C Cyan ink SBDEV976 | 35.31 | −17.08 | −59.43 |
| Ex. 4A Yellow ink SBDEV977 | 79.25 | 15.78 | 113.4 |

In order to have a comparative view, three standard Sun Chemical inks ELT series used for sensitive application (cigarette holder (filter)) and formulated with iron oxide pigments were selected: ELT-40020:ROJO BÁSICO (basic red)/ELT-20010:AMARILLO (yellow) 8001/A/ELT-90020: NEGRO BÁSICO (basic black).

TABLE 11

Colour property measurements of ELT iron oxide-based inks in TEST 9

| Inks/colour parameters | L* | a* | b* |
|---|---|---|---|
| Iron Oxide Black ELT | 9.43 | 0.92 | 2.73 |
| Iron Oxide Red ELT | 30.92 | 42.31 | 32.03 |
| Iron Oxide Yellow ELT | 68.34 | 20.82 | 63.9 |

Figure 7:
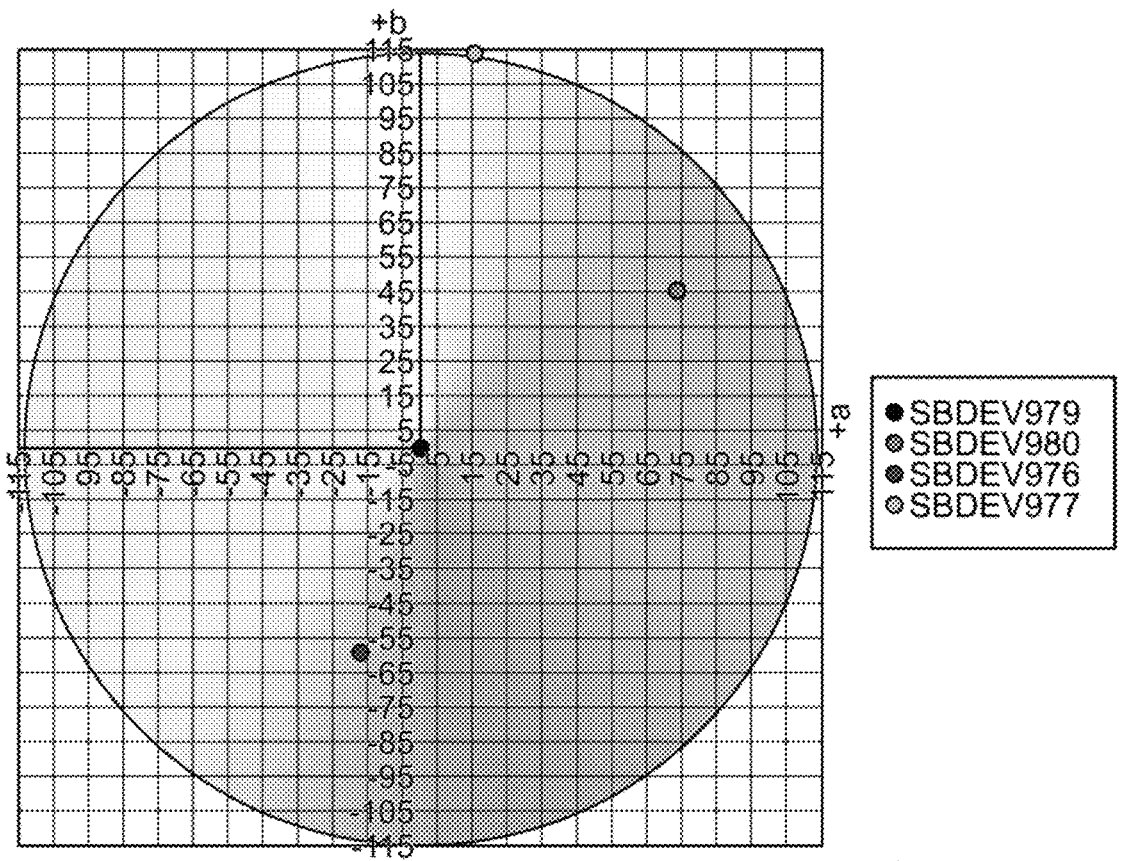
FIG. 7 shows the colour circle obtained with the yellow, red, cyan and black inks according to the invention that are suitable for direct food contact application.
Figure 8:
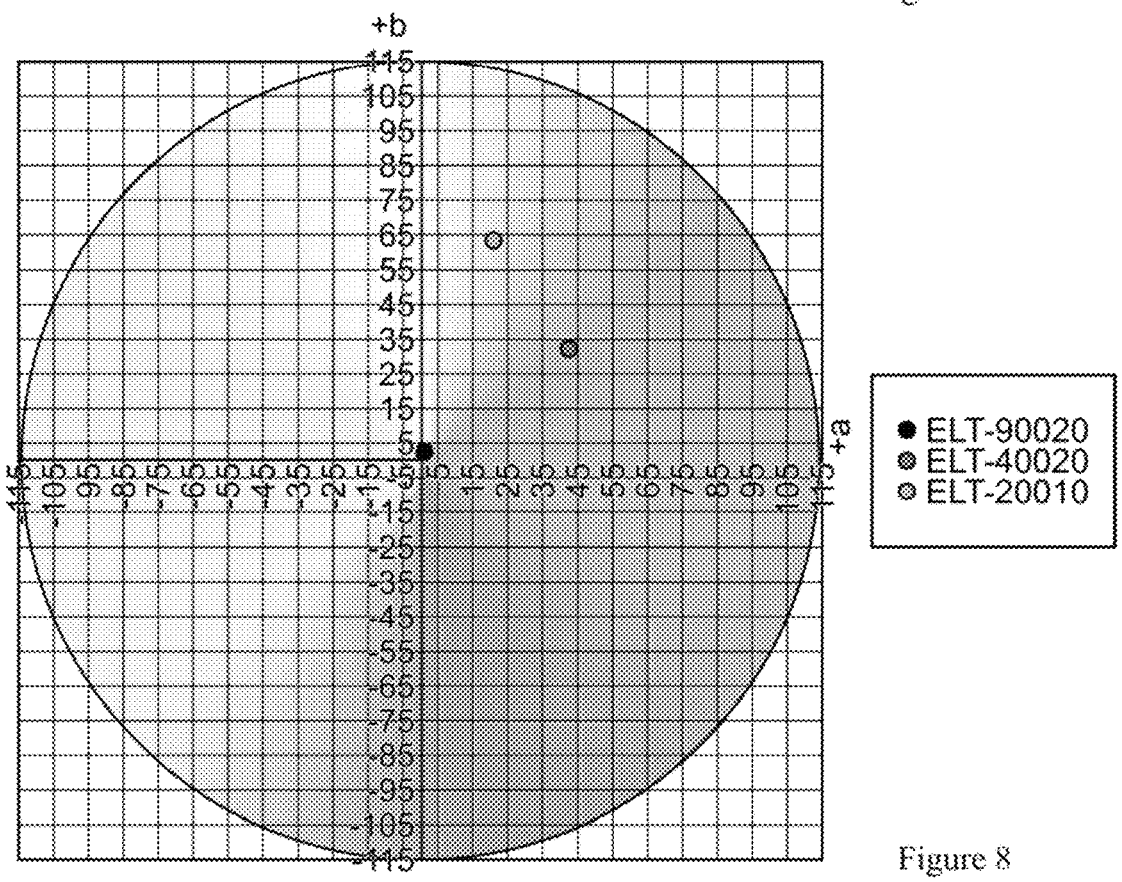
FIG. 8 shows the colour circle obtained with the comparative yellow, red and black ELT iron-oxide based inks.

The location of the four inventive inks within the colour circle is shown in FIG. 7 and the location of the three iron oxide based inks within the colour circle is shown in FIG. 8. As illustrated by FIGS. 7 and 8, the inventive inks have a much wider reach towards the perimeter of the colour circle.

Having established the corresponding colour parameters at these conditions for each of the SBDEV976, SBDEV977, SBDEV979 and SBDEV980 inks, the inventors calculated the colour gamut of the ink set (i.e. the SBDEV976, SBDEV977, SBDEV979 and SBDEV980 inks together) based on the primary L*, a*, b* values. For instance, colour gamut can be calculated using conventional software packages (the "Sun Chemical Gamut Viewer" software was used in this work) which create 3D models representing an estimated gamut shape and size of a set of measurements on a given substrate and printing process. Thus, the volume of the colour space contained in the gamut is calculated.

Figure 9:
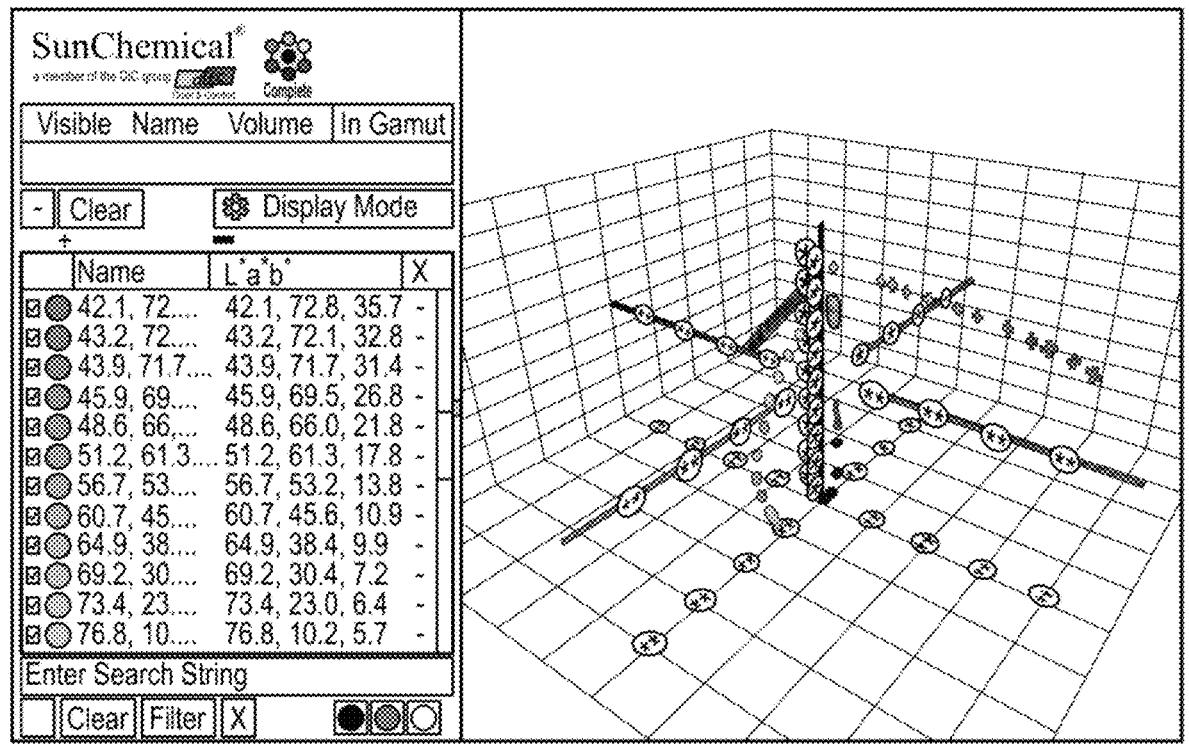
FIG. 9 shows the first step of the gamut estimation using Sun Chemical Gamut Viewer software.
Figure 10:
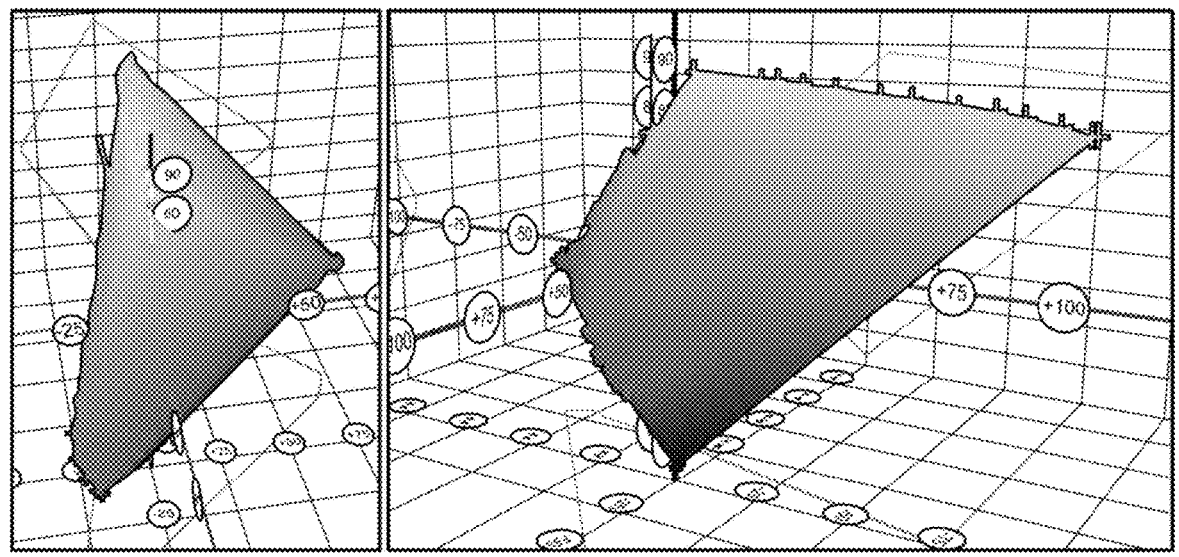
FIG. 10 shows the gamut view of the volume covered with the yellow, red, cyan and black inks according to the invention that are suitable for direct food contact application.

The first step of the gamut calculation is shown in FIG. 9, in which the L*a*b* values for each ink are plotted in the 3-dimensional CIELab colour space. The gamut view of the volume created by the SBDEV976, SBDEV977, SBDEV979 and SBDEV980 inventive inks is shown in FIG. 10.

Figure 11:
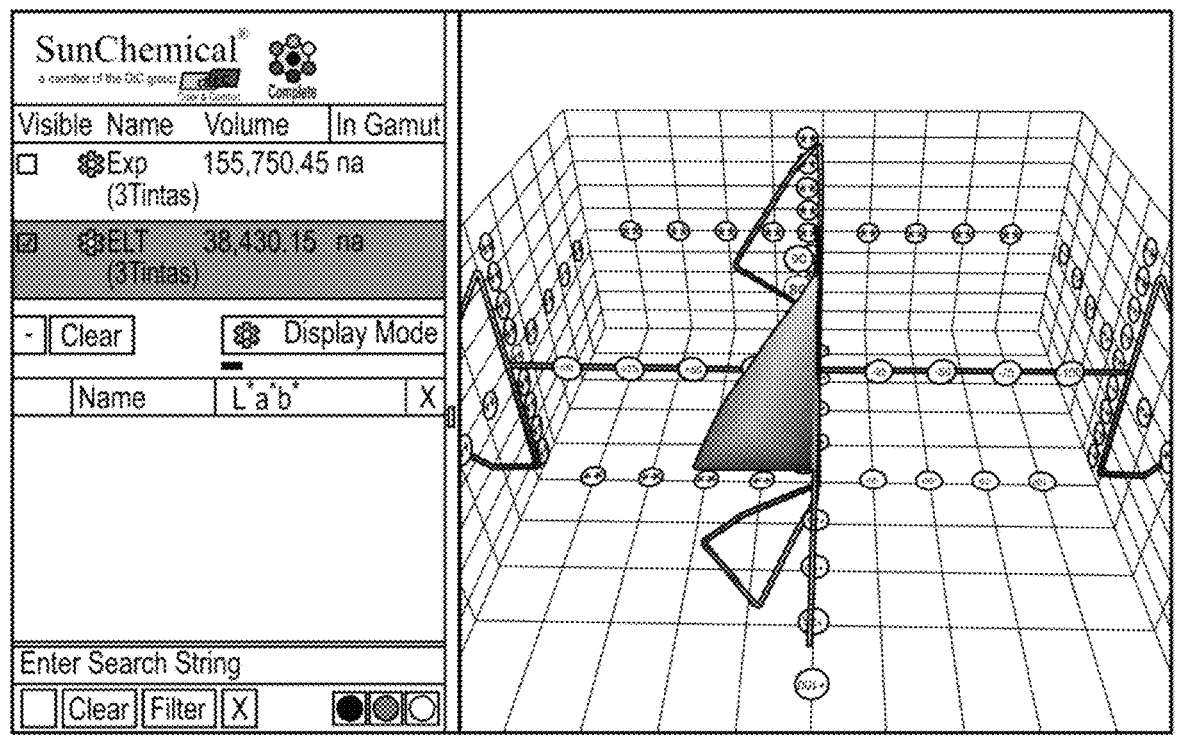
FIG. 11 shows the gamut view of the volume covered with the comparative yellow, red and black ELT iron-oxide based inks.
Figure 12:
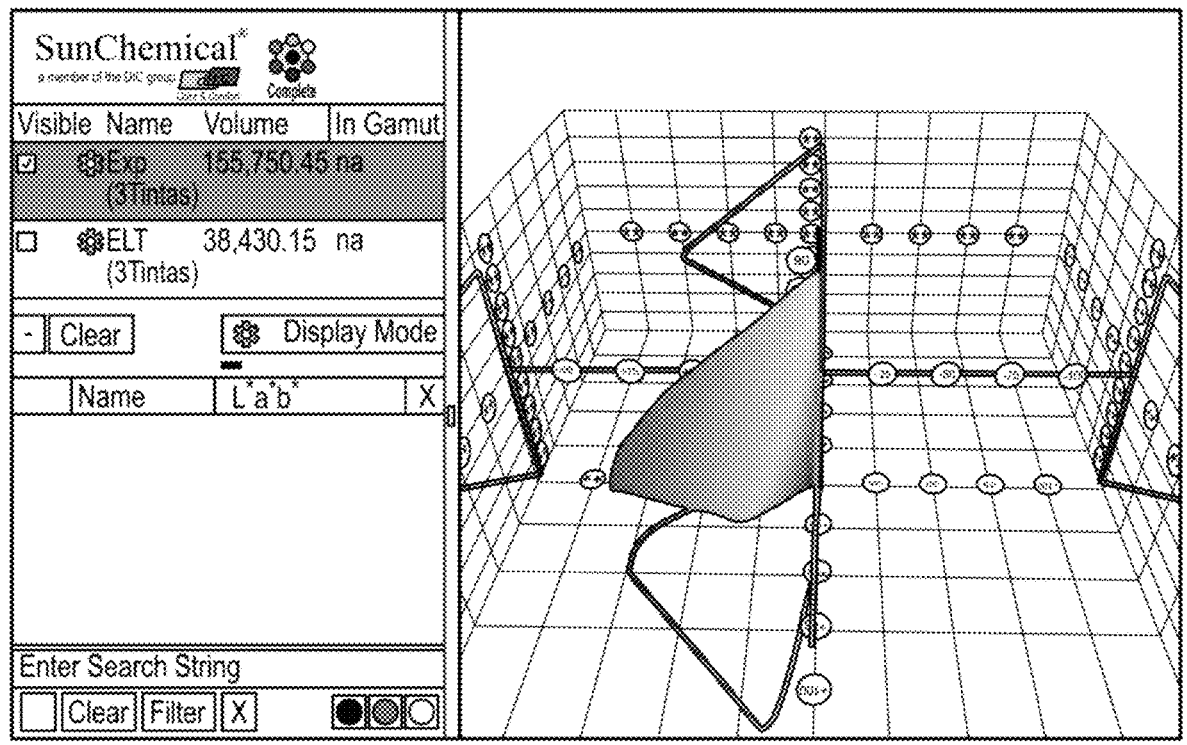
FIG. 12 shows the gamut view of the volume covered with the yellow, red and black inks according to the invention that are suitable for direct food contact application.

The colour gamut of the inventive inks can be compared with that of the iron oxide inks. In particular, the gamut volume created by the SBDEV976, SBDEV977, SBDEV979 and SBDEV980 inventive inks can be compared with the three iron oxide-based ELT inks (black, red and yellow) described above. The cyan SBDEV976 inventive ink is not considered in this comparison of the gamut volume in order to directly compare three inks according to the invention against three conventional inks. Thus, FIG. 11 shows the gamut view of the volume created by the three iron oxide-based inks, for which the gamut volume was calculated to be 38413 units. In contrast, FIG. 12 shows the gamut view of the volume created by the three inventive inks, for which the gamut volume was calculated to be 155750 units. Thus, the inventive inks create a volume in CIELab colourspace which is over 40% greater than that of the inks formulated with iron oxide pigments (155750 units vs 38413 units). As will be understood, by the skilled person, the units of gamut volume are CIELab L*, a*, b* colour cubes.

Safety for Direct Food Contact

The underlying requirement in the present invention is that the ink and coating compositions and substances contained therein should be safe for food contact, particularly direct food contact. The provision of ink and coating compositions according to the present invention is underpinned by a "Basis for Safety" outcome. This is based on an assumption that 100% of any given substance in an ink or coating composition migrates into the foodstuff, thereby allowing a "worst-case calculation" for the concentration of the substance in the foodstuff. Variables which affect the result of the worst-case calculation include (or may consist of) the concentration of each substance in the printing ink, the dry ink coating weight, the extent of coverage of the substrate surface with an ink on a % basis, the surface area of print in contact with food, and the weight of the food. The value of said variables are selected depending on the end-applications for which the compositions will be used. The values selected for each variable are reported in the exposure scenarios which are used for the safety determination. The resulting worse-case calculation is then compared to the specific migration limit (SML) for the substance. The principle of comparing specific migration limits with worst-case calculations is known in the art and described in Appendix D of "*Good Manufacturing Practice (GMP) Printing Inks for Food Contact Materials*" (4th Edition; March 2016; published by European Printing Ink Association). Using this methodology, one arrives at a Basis for Safety outcome, the possibilities for which are shown in Table 12:

TABLE 12

| Basis for Safety outomes | |
| --- | --- |
| Worst Case Calculation < SML | If 100% of the substance migrating into the food results in a level of migration that is below the Specific Migration Limit (SML), then there is no concern; the substance is safe for direct contact with food. This approach permits the safety of many substances to be determined without the need for migration testing. |
| Worst Case Calculation > SML Converter Review | If the Worst-Case Calculation would result in 100% of the substance migrating into the food at a level that is above the Specific Migration Limit (SML), then the substance needs to be subjected to migration testing to determine whether it is safe for DFC. |
| Converter Control | Some substances, such as solvents, are volatile and therefore evaporate during the ink drying process. Thus, the residual concentration of these substances in the dried ink film will be low. As the residual concentration of these substances is directly influenced by the actions of the converter (in how well the ink is dried), the converter can determine whether the drying process is fit for purpose. This can be done by subjecting such substances by migration testing. In the exemplified inks described hereinbelow, migration testing on such volatile substances revealed that the amounts thereof are not detectable. |

TABLE 12-continued

| Basis for Safety outomes | |
| --- | --- |
| | Thus, a converter of ordinary skill, following reasonable industry practices, will readily be able to reduce residual amounts to levels safe for DFC. |

In addition to the substance responsibly for the colour, many commercial products contain other chemicals (generally referred to as additives) that are present in order to improve the application properties of the product, such as the dispersibility, flow and flocculation resistance of pigments (dyes often contain significant amounts of diluents). In all cases, the essential colourant is the portion of the material responsible for the colour and excludes any additives.

Some substances, especially impurities and other non-intentionally-added-substances do not have published specific migration limits. For these substances it is important to ensure that they do not migrate at unsafe levels and that there is a basis of safety in using an ink containing these substances. The preferred basis for safety of such substances used in the provision of ink and coating compositions in the present invention is a hazard assessment-based approach, as discussed below.

The following publications, which are incorporated herein by reference, were relied upon for the Threshold of Toxicological Concern approach to hazard assessment developed by the European Food Safety Authority (EFSA), and in one instance, the World Health Organization (WHO):

1. EFSA Document: *Outcome of the public consultation on the draft guidance on the use of the Threshold of Toxicological Concern approach in food safety assessment*. APPROVED: 17 May 2019, doi:10.2903/sp.cfsa.2019.EN-1661;
2. EFSA Document: *Guidance on the use of the Threshold of Toxicological Concern approach in food safety assessment*, ADOPTED: 24 Apr. 2019, doi: 10.2903/j.efsa.2019.5708;
3. EFSA Document: *Priority topics for the development of risk assessment guidance by EFSA's Scientific Committee in 2016-2018*, ADOPTED: 19 May 2016, doi: 10.2903/j.efsa.2016.4502;
4. EFSA and WHO document: *Review of the Threshold of Toxicological Concern (TTC) approach and development of new TTC decision tree*. PUBLISHED: 10 Mar. 2016; and
5. EFSA Document: *Scientific Opinion on Exploring options for providing advice about possible human health risks based on the concept of Threshold of Toxicological Concern (TTC)*. EFSA Journal 2012; 10(7):2750

Preferably, the substance hazard assessment approach follows the process as set out in the EuPTA (European Printing Ink Trade Association) document: EuPTA Guidance for Risk Assessment of Non-Intentionally Added Substances (NIAS) and Non-Evaluated or Non-Listed Substances (NLS) in printing inks for food contact materials (May 2021). This approach in turn follows EFSA (European Food Safety Authority) methodology.

Preferably, the substance hazard assessment approach involves reviewing toxicological data to determine if the substance is genotoxic or has genotoxic potential. If there is no known toxicological data available for the substance then Qualitative Structure Activity Relationship (QSAR) toxicology prediction models are used to establish if the substance is genotoxic. In accordance with the EFSA "*Guidance on the use of the Threshold of Toxicology Concern approach in food safety assessment*" more than one model is used in the form of "read-across" from structurally similar chemicals. VEGA QSAR (version 1.1.5) was used in the present invention to establish genotoxicity. If a substance is not genotoxic it may be suitable for analysis using the Threshold for Toxicological Concern (TCC) approach and assigned a Cramer Class. If the absence of mutagenicity is the only information available then the applicable limit should be no more than Cramer Class III (corresponding to self-derived SML of up to 90 ppb).

The organic pigments used in the inks are not identified in the tables hereinbelow of potentially migrating substances, as it is not the organic pigments themselves that migrate, but rather other substances (residual starting substances, impurities, additives) that are present in the pigment. The pigments identified herein contain substances for which the risk of consumption is low.

Tables 13 and 14 below show how all of the materials chosen for the inks according to the present invention are within the guidelines for migration, even under strict conditions and worst-case scenarios that exceed the various regulatory requirements.

The data in Tables 13 and 14 include information on the substances present in the pigments and inks, including substance name, CAS number, the source of the specific migration limit or restriction, and the amount of substance permitted in food. Regulation (EU) No. 10/2011 (Annex 1) sets forth specific migration limits for the substances (see https://cur-lex.curopa.eu/legal-content/EN/TXT/HTML/?uri=CELEX:32011R0010&from=EN). Article 11 of this Regulation indicates that "For substances for which no specific migration limit or other restrictions are provided in Annex I, a generic specific migration limit of 60 mg/kg shall apply".

The inventors have demonstrated that, following the approach described above, the inks detailed in this invention are suitable for use in direct food contact applications. The level of substance being demonstrated by either worst-case calculation or by migration testing, and the hazard of the substance being demonstrated either by reference to regulatory positive lists or by substance hazard assessment.

Solvent-Based Direct Food Contact Exposure Scenarios

Figure 13A:
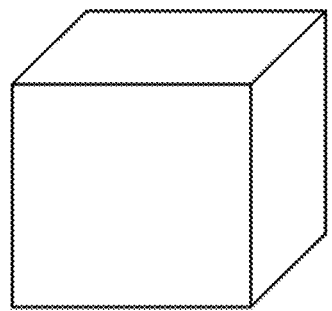
FIG. 13A is a depiction of a 10 cm×10 cm×10 cm cubic container representative of the presumed exposure in the EU cube exposure scenario for solvent-based direct food contact exposure.

The standard EU exposure scenario makes the assumption that 1 kg of food is consumed daily by a person of 60 kg bodyweight and that the food is packaged in a 10 cm×10 cm×10 cm cubic container, giving 1 kg of food wrapped in 0.06 m$^2$ of packaging (EU Regulation 10/2011; recitals 34 and 35), 100% of the interior surface of the cube is taken to be printed with the ink composition. This scenario is normally referred to as the EU Cube exposure scenario (see FIG. 13a). Having an exposure model such as the EU cube exposure scenario allows a Worst-Case Calculation for how much substance would migrate into 1 kg of food if all of the substance in the ink layer migrated into the food. Thus, the specific migration limits for the various substances recited in EU Regulation 10/2011 are therefore associated with the EU Cube exposure model.

Figure 13B:
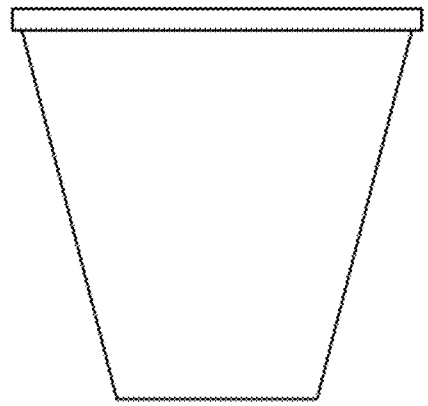
FIG. 13B represents a modification of the EU cube exposure scenario, wherein the container is a yoghurt pot, and the ink is printed onto the inside of the yoghurt pot lid.

However, real-world packaging and exposure scenarios often deviate from those of the EU Cube model, and so it is beneficial to consider other exposure scenarios described herein in which the ink or coating compositions described herein may be used and which differ significantly from the standard EU Cube model. Three such packaging applications that were created as part of the present invention are as follows:

Application 1. DFC ink printed onto inside of yoghurt pot lid (See FIG. 13b). In this scenario, the inside of the yoghurt lid is taken to be 100% printed with a DFC ink (although in reality the print coverage is likely to be less than this). The exposure can be compared to the standard EU Cube model, as follows:

Yoghurt pot lid diameter=6 cm. Area=28.3 cm$^2$=0.00283 m$^2$

Yoghurt pot weight of food=120 g=0.12 kg.

Yoghurt pot lid exposure scenario gives 1 kg food in contact with 0.0236 m$^2$ printed yoghurt lid.

This exposure scenario therefore gives approximately 39% of the exposure of the EU Cube.

Figure 13C:
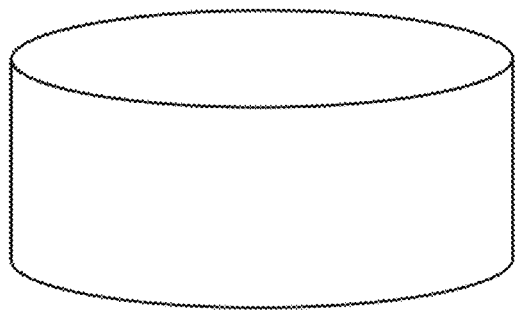
FIG. 13C represents a modification of the EU cube exposure scenario, wherein the container is a wrap covering the bottom and inside walls of cheese packaging, and the ink is printed on the wrap.

Application 2. DFC ink printed on a wrap covering the bottom and inside walls of cheese packaging (see FIG. 13c). In this scenario, the DFC-printed wrap is taken to be 100% printed with a DFC ink (although in reality the print coverage is likely to be less than this). The exposure can be compared to the standard EU Cube model, as follows:

Diameter of the cheese=11 cm, height of the cheese=3.5 cm.

Area of print in contact with cheese=216 cm$^2$=0.0216 m$^2$

Cheese food weight=250 g=0.25 kg

Cheese packaging exposure scenario gives 1 kg food in contact with 0.0864 m$^2$ printed wrap.

This exposure scenario therefore gives approximately 144% of the exposure of the EU Cube.

Figure 13D:
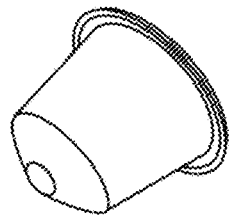
FIG. 13D represents a modification of the EU cube exposure scenario, wherein the container is a coffee capsule, and the ink is printed on the outside of the coffee capsule, coming into contact with the hot water used to make the coffee at the point where the coffee capsule is pierced.
Figure 13D:
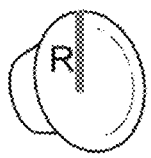
Figure 13D:
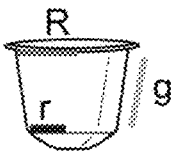
Figure 13D:
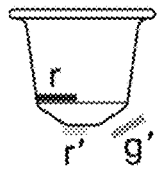
Figure 13D:
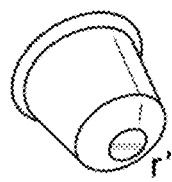

Application 3. DFC ink printed on the outside of a coffee capsule, coming into contact with the hot water used to make the coffee at the point where the coffee capsule is pierced. The outside of the capsule is taken to be 100% printed with the ink. See FIG. 13d for a calculation of the surface area. The exposure can be compared to the standard EU Cube model, as follows:

5.2 g of dried coffee produces 40 g to 100 g of wet coffee.

Coffee capsule exposure scenario gives between 1 kg coffee in contact with 0.0365 m$^2$ coffee capsule (100 g wet coffee) and 1 kg coffee in contact with 0.0913 m$^2$ coffee capsule (40 g wet coffee).

This exposure scenario gives between 61% and 152% of the exposure of the EU Cube.

A dry coat weight of 2.0 g/m$^2$ for the printed ink layer is adopted in all these exposure models.

Worst-Case Calculation (WCC) Data

As described hereinabove, the worst-case calculation assumes 100% migration of the substance to the foodstuff. Table 13 below presents the data generated according to the present invention, in which the worst-case calculation (WCC) is expressed as a percentage of the specific migration limit (SML; i.e. the maximum amount permitted) in each of the standard EU Cube model and Applications 1 to 3 above. In Table 13:

PR=EU Plastics Regulation No. 10/2011

HA=internal hazard assessment

FO=Swiss Ordinance (Ordinance on Materials and Articles (817.023.21) by the Food Safety and Veterinary Office (FSVO) of the Swiss Federal Department of Home Affairs (FDHA); latest version published 1 Dec. 2020)

Default=10 ppb

The SMLs, whether they are derived from the EU Plastics Regulation or from the Swiss Ordinance or are self-derived SMLs, are absolute values of the maximum amount (in mg) of a substance which is allowed to migrate into 1 kg food. Thus, SMLs are expressed in units of mg substance/kg food. SMLs are based on the toxicology of that substance. The SMLs referred to herein are all based on a regulatory assumption that a 60 kg adult consumes 1 kg of food per day and that the food is packaged in a cubic container (10 cm×10 cm×10 cm) which has a surface area of 6 dm² and which releases the substance into the food.

Extraction Testing

The substances in Table 13 were identified by extraction testing as follows. The raw materials were dissolved in several solvents to establish which solvent would be best to use for the analysis. Absolute ethanol and dichloromethane were found to be the best solvent for analysis. 0.1 g of each of the raw material samples were dissolved in 10 mL of absolute ethanol or dichloromethane with an internal standard of a known concentration added to each. The 10 mL extracts were sonicated at ambient temperature for 10 minutes to allow full dissolution of the raw material into the solvent. Once sonicated, 1 mL was taken from each raw material extract and syringe filtered using a 0.45 μm PTFE syringe filter into a 2 mL GC vial, ready for analysis on a GC-MS instrument. GC-MS was performed on a Thermo ISQ GC-MS system with a PTV injection port and a TG-5SILMS, 30 m column having 0.25 mm internal diameter and 0.25 μm thickness. The injection temperature was from 70° C. to 320° C. according to the table below:

| Temp. ramp (° C./min) | Temp. (° C.) | Time (min) |
| --- | --- | --- |
| — | 70 | 0.05 |
| 14.5 | 240 | 1.00 |
| 14.5 | 320 | 2.00 |

The GC oven temperature is increased from 45° C. to 320° C. (with a flow rate of 1 mL/min) according to the table below:

| Temp. ramp (° C./min) | Temp. (° C.) | Hold Time (min) |
| --- | --- | --- |
| — | 45 | 2 |
| 20 | 130 | 0 |
| 7.5 | 190 | 0 |
| 7.5 | 280 | 0 |
| 15 | 320 | 6 |

The data obtained from GC-MS was analysed using internal and NIST libraries and semi-quantified against the response of the internal standard. For the yellow pigment, a reference standard of tributyl phosphate was introduced and samples were re-analysed following calibration of the instrument to obtain more accurate quantitative results.

TABLE 13

| Product containing substance | CAS No of substance | Name of substance | SML (or restriction) (mg substance/kg food) | Source of SML or restriction | Amount of substance in product (wt %) | Amount of substance in dried film (wt %)[MIMI] |
| --- | --- | --- | --- | --- | --- | --- |
| SBDEV1284 | 0001333-86-4 | carbon black | 60 | PR | 8.998 | 38.085 |
| SBDEV1284 | 0009004-70-0 | nitrocellulose | 60 | PR | 1.742 | 7.373 |
| SBDEV1284 | 0009004-36-8 | cellulose acetate butyrate | 60 | PR | 1.600 | 6.772 |
| SBDEV1284 | 0007631-86-9 | silicon dioxide | 60 | PR | 1.000 | 4.232 |
| SBDEV1284 | 0009002-88-4 | polyethylene wax | 60 | PR | 0.500 | 2.116 |
| SBDEV1284 | 0008002-74-2 | waxes, refined, derived from petroleum based or synthetic hydrocarbon feedstocks, high viscosity | 60 | PR | 0.500 | 2.116 |
| SBDEV1284 | 0000128-37-0 | 2,6-Di-tert-butyl-p-cresol (=BHT) | 3 | PR | 0.256 | 1.083 |
| SBDEV1284 | 0004098-71-9 | IPDI (isophorone diisocyanate) | 1 | PR | 1.662 | 7.036 |
| SBDEV1284 | 0004744-11-0 | Propane, 1,1-dipropoxy- | 0.09 | HA | 0.355 | 1.501 |
| SBDEV1284 | 0000120-93-4 | 2-Imidazolidinone | 4.98 | HA | 0.102 | 0.432 |
| SBDEV1284 | 0002396-43-2 | 2,4,6-tripropyl-1,3,5-Trioxane | 0.09 | HA | 0.012 | 0.049 |
| SBDEV1284 | 0002051-50-5 | 2-Octyl acetate | 0.09 | HA | 0.002 | 0.008 |
| SBDEV1284 | 0000626-35-7 | Ethyl nitro acetate | 0.01 | Default 10 ppb | 0.001 | 0.003 |
| SBDEV1284 | 0000542-10-9 | Ethylidene diacetate | 0.09 | HA | 0.000 | 0.002 |
| SBDEV1284 | 0000498-60-2 | 3-furaldehyde | 0.09 | HA | 0.000 | 0.002 |
| SBDEV1284 | 0000077-90-7 | Tributyl acetyl citrate | 60 | PR | 0.012 | 0.049 |
| SBDEV1284 | 0000126-73-8 | Tributyl phosphate | 0.05 | SO | 0.000 | 0.000 |
| SBDEV1284 | 0000111-62-6 | Ethyl Oleate | 0.09 | HA | 0.004 | 0.017 |
| SBDEV1284 | 0000077-94-1 | Tributyl citrate | 0.05 | SO | 0.005 | 0.022 |
| SBDEV1284 | 0000071-23-8 | 1-propanol | 60 | PR | 11.682 | Converter Control |
| SBDEV1284 | 0000064-17-5 | ethanol | 60 | PR | 26.570 | Converter Control |
| SBDEV1284 | 0000141-78-6 | acetic acid, ethyl ester | 60 | PR | 29.865 | Converter Control |
| SBDEV1284 | 0000067-63-0 | 2-propanol | 60 | PR | 0.123 | Converter Control |
| SBDEV1284 | 0007732-18-5 | water | 60 | PR | 0.951 | Converter Control |

TABLE 13-continued

| | | | | | | |
|---|---|---|---|---|---|---|
| SBDEV1284 | 0000109-60-4 | Acetic acid, propyl ester | 60 | SO | 7.182 | Converter Control |
| SBDEV1285 | 0009004-70-0 | nitrocellulose | 60 | PR | 1.846 | 7.945 |
| SBDEV1285 | 0009004-36-8 | cellulose acetate butyrate | 60 | PR | 1.600 | 6.886 |
| SBDEV1285 | 0007631-86-9 | silicon dioxide | 60 | PR | 1.000 | 4.304 |
| SBDEV1285 | 0009002-88-4 | polyethylene wax | 60 | PR | 0.500 | 2.152 |
| SBDEV1285 | 0008002-74-2 | waxes, refined, derived from petroleum based or synthetic hydrocarbon feedstocks, high viscosity | 60 | PR | 0.500 | 2.152 |
| SBDEV1285 | 0000128-37-0 | 2,6-Di-tert-butyl-p-cresol (=BHT) | 3 | PR | 0.270 | 1.163 |
| SBDEV1285 | 0003815-20-1 | 4-Phenylbenzamide | 0.09 | HA | 0.040 | 0.171 |
| SBDEV1285 | No CAS | 2,4,6-Tris-Biphenyl-4-Yl-7H-Pyrolo[2,3-D]Pyrimidine-5-Carboxylic Acid | 0.01 | Default 10 ppb | 0.007 | 0.031 |
| SBDEV1285 | 0000104-88-1 | 4-Chlorobenzaldehyde | 0.09 | HA | 0.002 | 0.010 |
| SBDEV1285 | 0031274-51-8 | 1,3,5-Triazine, 2,4,6-Tris([1,1'-Biphenyl]-4-Yl)- | 5 | HA | 0.002 | 0.010 |
| SBDEV1285 | 0000092-92-2 | 4-Phenylbenzoic Acid | 0.09 | HA | 0.001 | 0.005 |
| SBDEV1285 | 0002920-38-9 | 4-Phenylbenzonitrile | 0.09 | HA | 0.001 | 0.003 |
| SBDEV1285 | 0153531-70-5 | Di-Isopropyl-Succinyl-Succinate | 0.09 | HA | 0.001 | 0.003 |
| SBDEV1285 | No CAS | 2,4-Bis-Biphenyl-4-Yl-Methyl-[1,3]Pyrimidene | 0.01 | Default 10 ppb | 0.000 | 0.002 |
| SBDEV1285 | 0003218-36-8 | 4-Phenylbenzaldehyde | 0.09 | HA | 0.000 | 0.001 |
| SBDEV1285 | 0004098-71-9 | IPDI (isophorone diisocyanate) | 1 | PR | 1.755 | 7.552 |
| SBDEV1285 | 0004744-11-0 | Propane, 1,1-dipropoxy- | 0.09 | HA | 0.374 | 1.611 |
| SBDEV1285 | 0000120-93-4 | 2-Imidazioldinone | 4.98 | HA | 0.108 | 0.464 |
| SBDEV1285 | 0002396-43-2 | 2,4,6-tripropyl-1,3,5-Trioxane | 0.09 | HA | 0.012 | 0.050 |
| SBDEV1285 | 0002051-50-5 | 2-Octyl acetate | 0.09 | HA | 0.002 | 0.008 |
| SBDEV1285 | 0000626-35-7 | Ethyl nitro acetate | 0.01 | Default 10 ppb | 0.001 | 0.003 |
| SBDEV1285 | 0000542-10-9 | Ethylidine diacetate | 0.09 | HA | 0.000 | 0.002 |
| SBDEV1285 | 0000498-60-2 | 3-Furaldehyde | 0.09 | HA | 0.000 | 0.002 |
| SBDEV1285 | 0000077-90-7 | Tributyl acetyl citrate | 60 | PR | 0.013 | 0.056 |
| SBDEV1285 | 0000126-73-8 | Tributyl phosphate | 0.05 | SO | 0.000 | 0.000 |
| SBDEV1285 | 0000111-62-6 | Ethyl Oleate | 0.09 | HA | 0.004 | 0.017 |
| SBDEV1285 | 0000077-94-1 | Tributyl citrate | 0.05 | SO | 0.005 | 0.022 |
| SBDEV1285 | 0000071-23-8 | 1-propanol | 60 | PR | 12.081 | Converter Control |
| SBDEV1285 | 0000064-17-5 | ethanol | 60 | PR | 27.841 | Converter Control |
| SBDEV1285 | 0000141-78-6 | acetic acid, ethyl ester | 60 | PR | 28.184 | Converter Control |
| SBDEV1285 | 0000067-63-0 | 2-propanol | 60 | PR | 0.129 | Converter Control |
| SBDEV1285 | 0007732-18-5 | water | 60 | PR | 0.949 | Converter Control |
| SBDEV1285 | 0000109-60-4 | Acetic acid, propyl ester | 60 | SO | 7.581 | Converter Control |
| SBDEV1286 | 0009004-70-0 | nitrocellulose | 60 | PR | 1.872 | 8.117 |
| SBDEV1286 | 0009004-36-8 | cellulose acetate butyrate | 60 | PR | 1.600 | 6.938 |
| SBDEV1286 | 0007631-86-9 | silicon dioxide | 60 | PR | 1.000 | 4.336 |
| SBDEV1286 | 0009002-88-4 | polyethylene wax | 60 | PR | 0.500 | 2.168 |
| SBDEV1286 | 0008002-74-2 | waxes, refined, derived from petroleum based or synthetic hydrocarbon feedstocks, high viscosity | 60 | PR | 0.500 | 2.168 |
| SBDEV1286 | 0000128-37-0 | 2,6-Di-tert-butyl-p-cresol (=BHT) | 3 | PR | 0.270 | 1.171 |

TABLE 13-continued

| | | | | | | |
|---|---|---|---|---|---|---|
| SBDEV1286 | 0000091-20-3 | Napthalene | 0.01 | Default 10 ppb | 0.000 | 0.000 |
| SBDEV1286 | 0064742-94-5 | Solvent naptha (petroleum), heavy arom. | 0.01 | SO | 0.003 | 0.014 |
| SBDEV1286 | 0004098-71-9 | IPDI (isophorone diisocyanate) | 1 | PR | 1.755 | 7.609 |
| SBDEV1286 | 0004744-11-0 | Propane, 1,1-dipropoxy- | 0.09 | HA | 0.374 | 1.623 |
| SBDEV1286 | 0000120-93-4 | 2-Imidazolidinone | 4.98 | HA | 0.108 | 0.467 |
| SBDEV1286 | 0002396-43-2 | 2,4,6-tripropyl-1,3,5-Trioxane | 0.09 | HA | 0.010 | 0.045 |
| SBDEV1286 | 0002051-50-5 | 2-Octyl acetate | 0.09 | HA | 0.002 | 0.009 |
| SBDEV1286 | 0000626-35-7 | Ethyl nitro acetate | 0.01 | Default 10 ppb | 0.001 | 0.003 |
| SBDEV1286 | 0000542-10-9 | Ethylidene diacetate | 0.09 | HA | 0.000 | 0.002 |
| SBDEV1286 | 0000498-60-2 | 3-Furaldehyde | 0.09 | HA | 0.000 | 0.002 |
| SBDEV1286 | 0000077-90-7 | Tributyl acetyl citrate | 60 | PR | 0.012 | 0.052 |
| SBDEV1286 | 0000126-73-8 | Tributyl phosphate | 0.05 | SO | 0.000 | 0.000 |
| SBDEV1286 | 0000111-62-6 | Ethyl Oleate | 0.09 | HA | 0.004 | 0.017 |
| SBDEV1286 | 0000077-94-1 | Tributyl citrate | 0.05 | SO | 0.005 | 0.022 |
| SBDEV1286 | 0000071-23-8 | 1-propanol | 60 | PR | 12.381 | Converter Control |
| SBDEV1286 | 0000064-17-5 | ethanol | 60 | PR | 26.198 | Converter Control |
| SBDEV1286 | 0000141-78-6 | acetic acid, ethyl ester | 60 | PR | 30.610 | Converter Control |
| SBDEV1286 | 0000067-63-0 | 2-propanol | 60 | PR | 0.120 | Converter Control |
| SBDEV1286 | 0007732-18-5 | water | 60 | PR | 0.045 | Converter Control |
| SBDEV1286 | 0000109-60-4 | Acetic acid, propyl ester | 60 | SO | 7.581 | Converter Control |
| SBDEV1286 | 0000100-41-4 | Ethylbenzene | 0.6 | SO | 0.000 | Converter Control |
| SBDEV1287 | 0009004-70-0 | nitrocellulose | 60 | PR | 1.677 | 7.354 |
| SBDEV1287 | 0009004-36-8 | cellulose acetate butyrate | 60 | PR | 1.600 | 7.017 |
| SBDEV1287 | 0007631-86-9 | silicon dioxide | 60 | PR | 1.000 | 4.385 |
| SBDEV1287 | 0009002-88-4 | polyethylene wax | 60 | PR | 0.500 | 2.193 |
| SBDEV1287 | 0008002-74-2 | waxes, refined, derived from petroleum based or synthetic hydrocarbon feedstocks, high viscosity | 60 | PR | 0.500 | 2.193 |
| SBDEV1287 | 0000128-37-0 | 2,6-Di-tert-butyl-p-cresol (=BHT) | 3 | PR | 0.246 | 1.081 |
| SBDEV1287 | 0000102-71-6 | triethanolamine | 0.05 | PR | 0.000 | 0.001 |
| SBDEV1287 | 0013481-50-0 | 2,4,6(1H,3H,5H)-Pyrimidinetrione, 5-(2,3-Dihydro-3-Oxo-1H-Isoindol-1-Ylidene)- | 0.09 | HA | 0.641 | 2.812 |
| SBDEV1287 | 0000067-52-7 | Barbituric acid | 0.09 | HA | 0.214 | 0.937 |
| SBDEV1287 | 0000085-41-6 | Phthalimide | 0.09 | HA | 0.162 | 0.712 |
| SBDEV1287 | 0004098-71-9 | IPDI (isophorone diisocyanate) | 1 | PR | 1.601 | 7.020 |
| SBDEV1287 | 0004744-11-0 | Propane, 1,1-dipropoxy- | 0.09 | HA | 0.342 | 1.498 |
| SBDEV1287 | 0000120-93-4 | 2-Imidazolidinone | 4.98 | HA | 0.098 | 0.431 |
| SBDEV1287 | 0002396-43-2 | 2,4,6-tripropyl-1,3,5-Trioxane | 0.09 | HA | 0.012 | 0.051 |
| SBDEV1287 | 0002051-50-5 | 2-Octyl acetate | 0.09 | HA | 0.002 | 0.008 |
| SBDEV1287 | 0000626-35-7 | Ethyl nitro acetate | 0.01 | Default 10 ppb | 0.001 | 0.003 |
| SBDEV1287 | 0000498-60-2 | 3-Furaldehyde | 0.09 | HA | 0.000 | 0.002 |
| SBDEV1287 | 0000542-10-9 | Ethylidene diacetate | 0.09 | HA | 0.000 | 0.002 |
| SBDEV1287 | 0000093-83-4 | N,N-Bis(2-hydroxyethyl) oleamide | 0.09 | HA | 0.641 | 2.812 |
| SBDEV1287 | 0000077-90-7 | Tributyl acetyl citrate | 60 | PR | 0.013 | 0.450 |
| SBDEV1287 | 0000126-73-8 | Tributyl phosphate | 0.05 | SO | 0.060 | 0.263 |
| SBDEV1287 | 0000111-62-6 | Ethyl Oleate | 0.09 | HA | 0.04 | 0.017 |
| SBDEV1287 | 0000077-94-1 | Tributyl citrate | 0.05 | SO | 0.005 | 0.022 |
| SBDEV1287 | 0000071-23-8 | 1-propanol | 60 | PR | 13.216 | Converter Control |

TABLE 13-continued

| | | | | | | |
|---|---|---|---|---|---|---|
| SBDEV1287 | 0000064-17-5 | ethanol | 60 | PR | 26.992 | Converter Control |
| SBDEV1287 | 0000141-78-6 | acetic acid, ethyl ester | 60 | PR | 28.956 | Converter Control |
| SBDEV1287 | 0000067-63-0 | 2-propanol | 60 | PR | 0.126 | Converter Control |
| SBDEV1287 | 0007732-18-5 | water | 60 | PR | 0.949 | Converter Control |
| SBDEV1287 | 0000109-60-4 | Acetic acid, propyl ester | 60 | SO | 6.916 | Converter Control |
| SBDEV1287 | 0000111-42-2 | Diethanolamine | 0.3 | SO | 0.043 | Converter Control |
| SBDEV1287 | 0000141-43-5 | 2-aminoethanol | 0.05 | PR | 0.000 | Converter Control |
| SBDEV976 | 0009004-36-8 | cellulose acetate butyrate | 60 | PR | 1.600 | 6.981 |
| SBDEV976 | 0009002-88-4 | polyethylene wax | 60 | PR | 0.500 | 2.182 |
| SBDEV976 | 0008002-74-2 | waxes, refined, derived from petroleum based or synthetic hydrocarbon feedstocks, high viscosity | 60 | PR | 0.500 | 2.182 |
| SBDEV976 | 0000128-37-0 | 2,6-Di-tert-butyl-p-cresol (=BHT) | 3 | PR | 0.367 | 1.603 |
| SBDEV976 | 0000091-20-3 | Naphthalene | 0.01 | Default 10 ppb | 0.000 | 0.000 |
| SBDEV976 | 0064742-94-5 | Solvent naphtha (petroleum), heavy arom. | 0.01 | SO | 0.003 | 0.014 |
| SBDEV976 | 0004098-71-9 | IPDI (isophorone diisocyanate) | 1 | PR | 2.386 | 10.410 |
| SBDEV976 | 0004744-11-0 | Propane, 1,1-dipropoxy- | 0.09 | HA | 0.509 | 2.221 |
| SBDEV976 | 0000120-93-4 | 2-Imidazolidinone | 4.98 | HA | 0.147 | 0.640 |
| SBDEV976 | 0002396-43-2 | 2,4,6-tripropyl-1,3,5-Trioxane | 0.09 | HA | 0.010 | 0.045 |
| SBDEV976 | 0000077-90-7 | Tributyl acetyl citrate | 60 | PR | 0.014 | 0.063 |
| SBDEV976 | 0000126-73-8 | Tributyl phosphate | 0.05 | SO | 0.000 | 0.000 |
| 0SBDEV976 | 0000111-62-6 | Ethyl Oleate | 0.09 | HA | 0.004 | 0.018 |
| SBDEV976 | 0000077-94-1 | Tributyl citrate | 0.05 | SO | 0.005 | 0.023 |
| SBDEV976 | 0000071-23-8 | 1-propanol | 60 | PR | 15.128 | Converter Control |
| SBDEV976 | 0000064-17-5 | ethanol | 60 | PR | 22.047 | Converter Control |
| SBDEV976 | 0000141-78-6 | acetic acid, ethyl ester | 60 | PR | 29.437 | Converter Control |
| SBDEV976 | 0000067-63-0 | 2-propanol | 60 | PR | 0.117 | Converter Control |
| SBDEV976 | 0007732-18-5 | water | 60 | PR | 0.044 | Converter Control |
| SBDEV976 | 0000109-60-4 | Acetic acid, propyl ester | 60 | SO | 10.308 | Converter Control |
| SBDEV976 | 0000100-41-4 | Ethylbenzene | 0.6 | SO | 0.000 | Converter Control |
| SBDEV977 | 0009004-36-8 | cellulose acetate butyrate | 60 | PR | 1.600 | 7.081 |
| SBDEV977 | 0009002-88-4 | polyethylene wax | 60 | PR | 0.500 | 2.213 |
| SBDEV977 | 0008002-74-2 | waxes, refined, derived from petroleum based or synthetic hydrocarbon feedstocks, high viscosity | 60 | PR | 0.500 | 2.213 |
| SBDEV977 | 0000128-37-0 | 2,6-Di-tert-butyl-p-cresol (=BHT) | 3 | PR | 0.335 | 1.484 |
| SBDEV977 | 0000102-71-6 | triethanolamine | 0.05 | PR | 0.000 | 0.001 |
| SBDEV977 | 0013481-50-0 | 2,4,6(1H,3H,5H)-Pyrimidinetrione, 5-(2,3-Dihydro-3-Oxo-1H-Isoindol-1-Ylidene)- | 0.09 | HA | 0.641 | 2.838 |
| SBDEV977 | 0000067-52-7 | Barbituric acid | 0.09 | HA | 0.214 | 0.946 |
| SBDEV977 | 0000085-41-6 | Phthalimide | 0.09 | HA | 0.162 | 0.719 |
| SBDEV977 | 0004098-71-9 | IPDI (isophorone diisocyanate) | 1 | PR | 2.178 | 9.640 |

TABLE 13-continued

| | | | | | | |
|---|---|---|---|---|---|---|
| SBDEV977 | 0004744-11-0 | Propane, 1,1-dipropoxy- | 0.09 | HA | 0.465 | 2.057 |
| SBDEV977 | 0000120-93-4 | 2-Imidazolidinone | 4.98 | HA | 0.134 | 0.592 |
| SBDEV977 | 0002396-43-2 | 2,4,6-tripropyl-1,3,5-Trioxane | 0.09 | HA | 0.011 | 0.050 |
| SBDEV977 | 0000093-83-4 | N,N-Bis(2-hydroxyethyl)oleamide | 0.09 | HA | 0.641 | 2.838 |
| SBDEV977 | 0000077-90-7 | Tributyl acetyl citrate | 60 | PR | 0.013 | 0.057 |
| SBDEV977 | 0000126-73-8 | Tributyl phosphate | 0.05 | SO | 0.060 | 0.266 |
| SBDEV977 | 0000111-62-6 | Ethyl Oleate | 0.09 | HA | 0.004 | 0.018 |
| SBDEV977 | 0000077-94-1 | Tributyl citrate | 0.05 | SO | 0.005 | 0.022 |
| SBDEV977 | 0000071-23-8 | 1-propanol | 60 | PR | 15.710 | Converter Control |
| SBDEV977 | 0000064-17-5 | ethanol | 60 | PR | 23.290 | Converter Control |
| SBDEV977 | 0000141-78-6 | acetic acid, ethyl ester | 60 | PR | 27.882 | Converter Control |
| SBDEV977 | 0000067-63-0 | 2-propanol | 60 | PR | 0.123 | Converter Control |
| SBDEV977 | 0007732-18-5 | water | 60 | PR | 0.948 | Converter Control |
| SBDEV977 | 0000109-60-4 | Acetic acid, propyl ester | 60 | SO | 9.410 | Converter Control |
| SBDEV977 | 0000111-42-2 | Diethanolamine | 0.3 | SO | 0.043 | Converter Control |
| SBDEV977 | 0000141-43-5 | 2-aminoethanol | 0.05 | PR | 0.000 | Converter Control |
| SBDEV979 | 0001333-86-4 | carbon black | 60 | PR | 8.998 | 38.376 |
| SBDEV979 | 0009004-36-8 | cellulose acetate butyrate | 60 | PR | 1.600 | 6.824 |
| SBDEV979 | 0009002-88-4 | polyethylene wax | 60 | PR | 0.500 | 2.132 |
| SBDEV979 | 0008002-74-2 | waxes, refined, derived from petroleum based or synthetic hydrocarbon feedstocks, high viscosity | 60 | PR | 0.500 | 2.132 |
| SBDEV979 | 0000128-37-0 | 2,6-Di-tert-butyl-p-cresol (=BHT) | 3 | PR | 0.348 | 1.485 |
| SBDEV979 | 0004098-71-9 | IPDI (isophorone diisocyanate) | 1 | PR | 2.261 | 9.644 |
| SBDEV979 | 0004744-11-0 | Propane, 1,1-dipropoxy- | 0.09 | HA | 0.482 | 2.058 |
| SBDEV979 | 0000120-93-4 | 2-Imidazolidinone | 4.98 | HA | 0.139 | 0.592 |
| SBDEV979 | 0002390-43-2 | 2,4,6-tripropyl-1,3,5-Trioxane | 0.09 | HA | 0.011 | 0.048 |
| SBDEV979 | 0000077-90-7 | Tributyl acetyl citrate | 60 | PR | 0.012 | 0.052 |
| SBDEV979 | 0000126-73-8 | Tributyl phosphate | 0.05 | SO | 0.000 | 0.000 |
| SBDEV979 | 0000111-62-6 | Ethyl Oleate | 0.09 | HA | 0.004 | 0.017 |
| SBDEV979 | 0000077-94-1 | Tributyl citrate | 0.05 | SO | 0.005 | 0.022 |
| SBDEV979 | 0000071-23-8 | 1-propanol | 60 | PR | 14.269 | Converter Control |
| SBDEV979 | 0000064-17-5 | ethanol | 60 | PR | 22.694 | Converter Control |
| SBDEV979 | 0000141-78-6 | acetic acid, ethyl ester | 60 | PR | 28.751 | Converter Control |
| SBDEV979 | 0000067-63-0 | 2-propanol | 60 | PR | 0.120 | Converter Control |
| SBDEV979 | 0007732-18-5 | water | 60 | PR | 0.950 | Converter Control |
| SBDEV979 | 0000109-60-4 | Acetic acid, propyl ester | 60 | SO | 9.769 | Converter Control |
| SBDEV980 | 0009004-36-8 | cellulose acetate butyrate | 60 | PR | 1.600 | 6.929 |
| SBDEV980 | 0009002-88-4 | polyethylene wax | 60 | PR | 0.500 | 2.165 |
| SBDEV980 | 0008002-74-2 | waxes, refined, derived from petroleum based or synthetic hydrocarbon feedstocks, high viscosity | 60 | PR | 0.500 | 2.165 |
| SBDEV980 | 0000128-37-0 | 2,6-Di-tert-butyl-p-cresol (=BHT) | 3 | PR | 0.367 | 1.590 |

TABLE 13-continued

| | | | | | | |
|---|---|---|---|---|---|---|
| SBDEV980 | 0003815-20-1 | 4-Phenylbenzamide | 0.09 | HA | 0.040 | 0.172 |
| SBDEV980 | No CAS | 2,4,6-Tris-Biphenyl-4-Yl-7H-Pyrrolo[2,3-D]Pyrimidine-5-Carboxylic Acid | 0.01 | Default 10 ppb | 0.007 | 0.032 |
| SBDEV980 | 0000104-88-1 | 4-Chlorobenzaldehyde | 0.09 | HA | 0.002 | 0.010 |
| SBDEV980 | 0031274-51-8 | 1,3,5-Triazine, 2,4,6-Tris([1,1'-Biphenyl]-4-Yl)- | 5 | HA | 0.002 | 0.010 |
| SBDEV980 | 0000092-92-2 | 4-Phenylbenzoic Acid | 0.09 | HA | 0.001 | 0.005 |
| SBDEV980 | 0002920-38-9 | 4-Phenylbenzonitrile | 0.09 | HA | 0.001 | 0.003 |
| SBDEV980 | 0153531-70-5 | Di-Isopropyl-Succinyl-Succinate | 0.09 | HA | 0.001 | 0.003 |
| SBDEV980 | No CAS | 2,4-Bis-Biphenyl-4-Yl-6-Methyl-[1,3]Pyrimidene | 0.01 | Default 10 ppb | 0.000 | 0.002 |
| SBDEV980 | 0003218-36-8 | 4-Phenylbenzaldehyde | 0.09 | HA | 0.000 | 0.001 |
| SBDEV980 | 0004098-71-9 | IPDI (isophorone diisocyanate) | 1 | PR | 2.386 | 10.332 |
| SBDEV980 | 0004744-11-0 | Propane, 1,1-dipropoxy- | 0.09 | HA | 0.509 | 2.204 |
| SBDEV980 | 0000120-93-4 | 2-Imidazolidinone | 4.98 | HA | 0.147 | 0.635 |
| SBDEV980 | 0002396-43-2 | 2,4,6-tripropyl-1,3,5-Trioxane | 0.09 | HA | 0.011 | 0.049 |
| SBDEV980 | 0000077-90-7 | Tributyl acetyl citrate | 60 | PR | 0.013 | 0.058 |
| SBDEV980 | 0000126-73-8 | Tributyl phosphate | 0.05 | SO | 0.000 | 0.000 |
| SBDEV980 | 0000111-62-6 | Ethyl Oleate | 0.09 | HA | 0.004 | 0.018 |
| SBDEV980 | 0000077-94-1 | Tributyl citrate | 0.05 | SO | 0.005 | 0.022 |
| SBDEV980 | 0000071-23-8 | 1-propanol | 60 | PR | 14.808 | Converter Control |
| SBDEV980 | 0000064-17-5 | ethaol | 60 | PR | 23.715 | Converter Control |
| SBDEV980 | 0000141-78-6 | acetic acid, ethyl ester | 60 | PR | 27.005 | Converter Control |
| SBDEV980 | 0000067-63-0 | 2-propanol | 60 | PR | 0.125 | Converter Control |
| SBDEV980 | 0007732-18-5 | water | 60 | PR | 0.948 | Converter Control |
| SBDEV980 | 0000109-60-4 | Acetic acid, propyl ester | 60 | SO | 10.308 | Converter Control |

| | | Worst-case calculation as a percentage of SML (or restriction) | | | | |
|---|---|---|---|---|---|---|
| Product containing substance | CAS No of substance | EU Cube | Application 1 | Application 2 | Application 3 (0.0365 m2 packaging) | Application 3 (0.0913 m2 packaging) |
| SBDEV1284 | 0001333-86-4 | 77 | 30.3 | *110.9* | 46.8 | *117.2* |
| SBDEV1284 | 0009004-70-0 | 15 | 5.9 | *21.6* | 9.1 | *22.8* |
| SBDEV1284 | 0009004-36-8 | 14 | 5.5 | 20.2 | 8.5 | 21.3 |
| SBDEV1284 | 0007631-86-9 | 9 | 3.5 | 13.0 | 5.5 | 13.7 |
| SBDEV1284 | 0009002-88-4 | 5 | 2.0 | 7.2 | 3.0 | 7.6 |
| SBDEV1284 | 0008002-74-2 | 5 | 2.0 | 7.2 | 3.0 | 7.6 |
| SBDEV1284 | 0000128-37-0 | 44 | 17.3 | 63.4 | 26.8 | 67.0 |
| SBDEV1284 | 0004098-71-9 | *850* | *334.3* | *1224.0* | *517.1* | *1293.4* |
| SBDEV1284 | 0004744-11-0 | *2100* | *826.0* | *3024.0* | *1277.5* | *3195.5* |
| SBDEV1284 | 0000120-93-4 | 11 | 4.3 | 15.8 | 6.7 | 16.7 |
| SBDEV1284 | 0002396-43-2 | 66 | 26.0 | 95.0 | 40.2 | *100.4* |
| SBDEV1284 | 0002051-50-5 | 11 | 4.3 | 15.8 | 6.7 | 16.7 |
| SBDEV1284 | 0000626-35-7 | 32 | 12.6 | 46.1 | 19.5 | 48.7 |
| SBDEV1284 | 0000542-10-9 | 3 | 1.2 | 4.3 | 1.8 | 4.6 |
| SBDEV1284 | 0000498-60-2 | 3 | 1.2 | 4.3 | 1.8 | 4.6 |
| SBDEV1284 | 0000077-90-7 | 0.05 | 0.17 | 0.07 | 0.18 | 0.05 |
| SBDEV1284 | 0000126-73-8 | 0 | 0 | 0 | 0 | 0 |
| SBDEV1284 | 0000111-62-6 | 22.7 | 8.91 | 32.68 | 13.82 | 34.55 |
| SBDEV1284 | 0000077-94-1 | 52.8 | 20.73 | 76.01 | 32.14 | 80.36 |
| SBDEV1284 | 0000071-23-8 | Converter Control | Converter Control | Converter Control | Converter Control | Converter Control |
| SBDEV1284 | 0000064-17-5 | Converter Control | Converter Control | Converter Control | Converter Control | Converter Control |
| SBDEV1284 | 0000141-78-6 | Converter Control | Converter Control | Converter Control | Converter Control | Converter Control |
| SBDEV1284 | 0000067-63-0 | Converter Control | Converter Control | Converter Control | Converter Control | Converter Control |

TABLE 13-continued

| | | | | | | |
|---|---|---|---|---|---|---|
| SBDEV1284 | 0007732-18-5 | Converter Control | Converter Control | Converter Control | Converter Control | Converter Control |
| SBDEV1284 | 0000109-60-4 | Converter Control | Converter Control | Converter Control | Converter Control | Converter Control |
| SBDEV1285 | 0009004-70-0 | 16 | 6.3 | 23.0 | 9.7 | 24.3 |
| SBDEV1285 | 0009004-36-8 | 14 | 5.5 | 20.2 | 8.5 | 21.3 |
| SBDEV1285 | 0007631-86-9 | 9 | 3.5 | 13.0 | 5.5 | 13.7 |
| SBDEV1285 | 0009002-88-4 | 5 | 2.0 | 7.2 | 3.0 | 7.6 |
| SBDEV1285 | 0008002-74-2 | 5 | 2.0 | 7.2 | 3.0 | 7.6 |
| SBDEV1285 | 0000128-37-0 | 47 | 18.5 | *67.7* | *28.6* | *71.5* |
| SBDEV1285 | 0003815-20-1 | *230* | *90.5* | *331.2* | *139.9* | *350.0* |
| SBDEV1285 | No CAS | *380* | *149.5* | *547.2* | *231.2* | *578.2* |
| SBDEV1285 | 0000104-88-1 | 14 | 5.5 | 20.2 | 8.5 | 21.3 |
| SBDEV1285 | 0031274-51-8 | 0.3 | 0.1 | 0.4 | 0.2 | 0.5 |
| SBDEV1285 | 0000092-92-2 | 7 | 2.8 | 10.1 | 4.3 | 10.7 |
| SBDEV1285 | 0002920-38-9 | 5 | 2.0 | 7.2 | 3.0 | 7.6 |
| SBDEV1285 | 0153531-70-5 | 5 | 2.0 | 7.2 | 3.0 | 7.6 |
| SBDEV1285 | No CAS | 21 | 8.3 | 30.2 | 12.8 | 32.0 |
| SBDEV1285 | 0003218-36-8 | 0.9 | 0.4 | 1.3 | 0.5 | 1.4 |
| SBDEV1285 | 0004098-71-9 | *910* | *357.9* | *1310.4* | *553.6* | *1384.7* |
| SBDEV1285 | 0004744-11-0 | *2200* | *865.3* | *3168.0* | *1338.3* | *3347.7* |
| SBDEV1285 | 0000120-93-4 | 12 | 4.7 | 17.3 | 7.3 | 18.3 |
| SBDEV1285 | 0002396-43-2 | 67 | 26.4 | 96.5 | 40.8 | *102.0* |
| SBDEV1285 | 0002051-50-5 | 12 | 4.7 | 17.3 | 7.3 | 18.3 |
| SBDEV1285 | 0000626-35-7 | 34 | 13.4 | 49.0 | 20.7 | 51.7 |
| SBDEV1285 | 0000542-10-9 | 3 | 1.2 | 4.3 | 1.8 | 4.6 |
| SBDEV1285 | 0000498-60-2 | 3 | 1.2 | 4.3 | 1.8 | 4.6 |
| SBDEV1285 | 0000077-90-7 | 0.11 | 0.04 | 0.16 | 0.07 | 0.17 |
| SBDEV1285 | 0000126-73-8 | 0 | 0 | 0 | 0 | 0 |
| SBDEV1285 | 0000111-62-6 | 22.7 | 8.91 | 32.68 | 13.82 | 34.55 |
| SBDEV1285 | 0000077-94-1 | 52.8 | 20.73 | 76.01 | 32.14 | 80.36 |
| SBDEV1285 | 0000071-23-8 | Converter Control | Converter Control | Converter Control | Converter Control | Converter Control |
| SBDEV1285 | 0000064-17-5 | Converter Control | Converter Control | Converter Control | Converter Control | Converter Control |
| SBDEV1285 | 0000141-78-6 | Converter Control | Converter Control | Converter Control | Converter Control | Converter Control |
| SBDEV1285 | 0000067-63-0 | Converter Control | Converter Control | Converter Control | Converter Control | Converter Control |
| SBDEV1285 | 0007732-18-5 | Converter Control | Converter Control | Converter Control | Converter Control | Converter Control |
| SBDEV1285 | 0000109-60-4 | Converter Control | Converter Control | Converter Control | Converter Control | Converter Control |
| SBDEV1286 | 0009004-70-0 | 17 | 6.7 | 24.5 | 10.3 | 25.9 |
| SBDEV1286 | 0009004-36-8 | 14 | 5.5 | 20.2 | 8.5 | 21.3 |
| SBDEV1286 | 0007631-86-9 | 9 | 3.5 | 13.0 | 5.5 | 13.7 |
| SBDEV1286 | 0009002-88-4 | 5 | 2.0 | 7.2 | 3.0 | 7.6 |
| SBDEV1286 | 0008002-74-2 | 5 | 2.0 | 7.2 | 3.0 | 7.6 |
| SBDEV1286 | 0000128-37-0 | 47 | 18.5 | 67.7 | 28.6 | 71.5 |
| SBDEV1286 | 0000091-20-3 | 0.4 | 0.2 | 0.6 | 0.2 | 0.6 |
| SBDEV1286 | 0064742-94-5 | *170* | *66.9* | *244.8* | *103.4* | *258.7* |
| SBDEV1286 | 0004098-71-9 | *920* | *361.9* | *1324.8* | *559.7* | *1399.9* |
| SBDEV1286 | 0004744-11-0 | *2200* | *865.3* | *3168.0* | *1338.3* | *3347.7* |
| SBDEV1286 | 0000120-93-4 | 12 | 4.7 | 17.3 | 7.3 | 18.3 |
| SBDEV1286 | 0002396-43-2 | 61 | 24.0 | 87.8 | 37.1 | 92.8 |
| SBDEV1286 | 0002051-50-5 | 12 | 4.7 | 17.3 | 7.3 | 18.3 |
| SBDEV1286 | 0000626-35-7 | 35 | 13.8 | 50.4 | 21.3 | 53.3 |
| SBDEV1286 | 0000542-10-9 | 3 | 1.2 | 4.3 | 1.8 | 4.6 |
| SBDEV1286 | 0000498-60-2 | 3 | 1.2 | 4.3 | 1.8 | 4.6 |
| SBDEV1286 | 0000077-90-7 | 0.10 | 0.04 | 0.14 | 0.06 | 0.15 |
| SBDEV1286 | 0000126-73-8 | 0 | 0 | 0 | 0 | 0 |
| SBDEV1286 | 0000111-62-6 | 22.7 | 8.91 | 32.68 | 13.82 | 34.55 |
| SBDEV1286 | 0000077-94-1 | 52.8 | 20.73 | 76.01 | 32.14 | 80.36 |
| SBDEV1286 | 0000071-23-8 | Converter Control | Converter Control | Converter Control | Converter Control | Converter Control |
| SBDEV1286 | 0000064-17-5 | Converter Control | Converter Control | Converter Control | Converter Control | Converter Control |
| SBDEV1286 | 0000141-78-6 | Converter Control | Converter Control | Converter Control | Converter Control | Converter Control |
| SBDEV1286 | 0000067-63-0 | Converter Control | Converter Control | Converter Control | Converter Control | Converter Control |
| SBDEV1286 | 0007732-18-5 | Converter Control | Converter Control | Converter Control | Converter Control | Converter Control |
| SBDEV1286 | 0000109-60-4 | Converter Control | Converter Control | Converter Control | Converter Control | Converter Control |
| SBDEV1286 | 0000100-41-4 | Converter Control | Converter Control | Converter Control | Converter Control | Converter Control |
| SBDEV1287 | 0009004-70-0 | 15 | 5.9 | 21.6 | 9.1 | 22.8 |
| SBDEV1287 | 0009004-36-8 | 15 | 5.9 | 21.6 | 9.1 | 22.8 |
| SBDEV1287 | 0007631-86-9 | 9 | 3.54 | 13.0 | 5.5 | 13.7 |

TABLE 13-continued

| | | | | | | |
|---|---|---|---|---|---|---|
| SBDEV1287 | 0009002-88-4 | 5 | 2.0 | 7.2 | 3.0 | 7.6 |
| SBDEV1287 | 0008002-74-2 | 5 | 2.0 | 7.2 | 3.0 | 7.6 |
| SBDEV1287 | 0000128-37-0 | 44 | 17.3 | 63.4 | 26.8 | 67.0 |
| SBDEV1287 | 0000102-71-6 | 2 | 0.8 | 2.9 | 1.2 | 3.0 |
| SBDEV1287 | 0013481-50-0 | *3800* | *1494.7* | *5472.0* | *2311.7* | *5782.3* |
| SBDEV1287 | 0000067-52-7 | *1300* | *511.3* | *1872.0* | *790.8* | *1978.2* |
| SBDEV1287 | 0000085-41-6 | *950* | *373.7* | *1368.0* | *577.9* | *1445.6* |
| SBDEV1287 | 0004098-71-9 | *850* | *334.3* | *1224.0* | *517.1* | *1293.4* |
| SBDEV1287 | 0004744-11-0 | *2000* | *786.7* | *2880.0* | *1216.7* | *3043.3* |
| SBDEV1287 | 0000120-93-4 | 11 | 4.3 | 15.8 | 6.7 | *16.7* |
| SBDEV1287 | 0002396-43-2 | 68 | 26.7 | 97.9 | 41.4 | *103.5* |
| SBDEV1287 | 0002051-50-5 | 11 | 4.3 | 15.8 | 6.7 | *16.7* |
| SBDEV1287 | 0000626-35-7 | 33 | 13.0 | 47.5 | 20.1 | 50.2 |
| SBDEV1287 | 0000498-60-2 | 3 | 1.2 | 4.3 | 1.8 | 4.6 |
| SBDEV1287 | 0000542-10-9 | 3 | 1.2 | 4.3 | 1.8 | 4.6 |
| SBDEV1287 | 0000093-83-4 | 68 | 26.7 | 97.9 | 41.4 | *103.5* |
| SBDEV1287 | 0000077-90-7 | 0.90 | 0.04 | 1.30 | 0.54 | *1.40* |
| SBDEV1287 | 0000126-73-8 | 631.2 | 247.8 | 908.7 | 384.2 | *960.7* |
| SBDEV1287 | 0000111-62-6 | 22.7 | 8.91 | 32.68 | 13.82 | *34.55* |
| SBDEV1287 | 0000077-94-1 | 52.8 | 20.73 | 76.01 | 32.14 | *80.36* |
| SBDEV1287 | 0000071-23-8 | Converter Control | Converter Control | Converter Control | Converter Control | Converter Control |
| SBDEV1287 | 0000064-17-5 | Converter Control | Converter Control | Converter Control | Converter Control | Converter Control |
| SBDEV1287 | 0000141-78-6 | Converter Control | Converter Control | Converter Control | Converter Control | Converter Control |
| SBDEV1287 | 0000067-63-0 | Converter Control | Converter Control | Converter Control | Converter Control | Converter Control |
| SBDEV1287 | 0007732-18-5 | Converter Control | Converter Control | Converter Control | Converter Control | Converter Control |
| SBDEV1287 | 0000109-60-4 | Converter Control | Converter Control | Converter Control | Converter Control | Converter Control |
| SBDEV1287 | 0000111-42-2 | Converter Control | Converter Control | Converter Control | Converter Control | Converter Control |
| SBDEV1287 | 0000141-43-5 | Converter Control | Converter Control | Converter Control | Converter Control | Converter Control |
| SBDEV976 | 0009004-36-8 | 14 | 5.5 | 20.2 | 8.5 | 21.3 |
| SBDEV976 | 0009002-88-4 | 5 | 2.0 | 7.2 | 3.0 | 7.6 |
| SBDEV976 | 0008002-74-2 | 5 | 2.0 | 7.2 | 3.0 | 7.6 |
| SBDEV976 | 0000128-37-0 | 65 | 25.6 | 93.6 | 39.5 | 98.9 |
| SBDEV976 | 0000091-20-3 | 0.4 | 0.2 | 0.6 | 0.2 | 0.6 |
| SBDEV976 | 0064742-94-5 | *170* | *66.9* | *244.8* | *103.4* | *258.7* |
| SBDEV976 | 0004098-71-9 | *1300* | *511.3* | *1872.0* | *790.8* | *1978.2* |
| SBDEV976 | 0004744-11-0 | *3000* | *1180.0* | *4320.0* | *1825.0* | *4565.0* |
| SBDEV976 | 0000120-93-4 | 16 | 6.3 | 23.0 | 9.7 | 24.3 |
| SBDEV976 | 0002396-43-2 | 61 | 24.0 | 87.8 | 37.1 | 92.8 |
| SBDEV976 | 0000077-90-7 | 0.12 | 0.05 | 0.17 | 0.07 | 0.18 |
| SBDEV976 | 0000126-73-8 | 0 | 0 | 0 | 0 | 0 |
| 0SBDEV976 | 0000111-62-6 | 24.0 | 9.42 | 34.6 | 14.6 | 36.5 |
| SBDEV976 | 0000077-94-1 | 55.2 | 21.7 | 79.6 | 33.6 | 83.9 |
| SBDEV976 | 0000071-23-8 | Converter Control | Converter Control | Converter Control | Converter Control | Converter Control |
| SBDEV976 | 0000064-17-5 | Converter Control | Converter Control | Converter Control | Converter Control | Converter Control |
| SBDEV976 | 0000141-78-6 | Converter Control | Converter Control | Converter Control | Converter Control | Converter Control |
| SBDEV976 | 0000067-63-0 | Converter Control | Converter Control | Converter Control | Converter Control | Converter Control |
| SBDEV976 | 0007732-18-5 | Converter Control | Converter Control | Converter Control | Converter Control | Converter Control |
| SBDEV976 | 0000109-60-4 | Converter Control | Converter Control | Converter Control | Converter Control | Converter Control |
| SBDEV976 | 0000100-41-4 | Converter Control | Converter Control | Converter Control | Converter Control | Converter Control |
| SBDEV977 | 0009004-36-8 | 15 | 5.9 | 21.6 | 9.1 | 22.8 |
| SBDEV977 | 0009002-88-4 | 5 | 2.0 | 7.2 | 3.0 | 7.6 |
| SBDEV977 | 0008002-74-2 | 5 | 2.0 | 7.2 | 3.0 | 7.6 |
| SBDEV977 | 0000128-37-0 | 60 | 23.6 | 86.4 | 36.5 | 91.3 |
| SBDEV977 | 0000102-71-6 | 2 | 0.8 | 2.9 | 1.2 | 3.0 |
| SBDEV977 | 0013481-50-0 | *3800* | *1494.7* | *5472.0* | *2311.7* | *5782.3* |
| SBDEV977 | 0000067-52-7 | *1300* | *511.3* | *1872.0* | *790.8* | *1978.2* |
| SBDEV977 | 0000085-41-6 | *960* | *377.6* | *1382.4* | *584.0* | *1460.8* |
| SBDEV977 | 0004098-71-9 | *1200* | *472.0* | *1728.0* | *730.0* | *1826.0* |
| SBDEV977 | 0004744-11-0 | *2800* | *1101.3* | *4032.0* | *1703.3* | *4260.7* |
| SBDEV977 | 0000120-93-4 | 15 | 5.9 | 21.6 | 9.1 | 22.8 |
| SBDEV977 | 0002396-43-2 | 67 | 26.4 | 96.5 | 40.8 | *102.0* |
| SBDEV977 | 0000093-83-4 | 69 | 27.1 | 99.4 | 42.0 | *105.0* |
| SBDEV977 | 0000077-90-7 | 0.11 | 0.04 | 0.16 | 0.07 | *0.17* |
| SBDEV977 | 0000126-73-8 | 638.4 | 250.7 | 919.7 | 388.6 | *971.5* |
| SBDEV977 | 0000111-62-6 | 24.0 | 9.42 | 34.6 | 14.6 | *36.5* |

TABLE 13-continued

| | | | | | | |
|---|---|---|---|---|---|---|
| SBDEV977 | 0000077-94-1 | 53.2 | 20.9 | 76.7 | 32.4 | _80.9_ |
| SBDEV977 | 0000071-23-8 | Converter Control | Converter Control | Converter Control | Converter Control | Converter Control |
| SBDEV977 | 0000064-17-5 | Converter Control | Converter Control | Converter Control | Converter Control | Converter Control |
| SBDEV977 | 0000141-78-6 | Converter Control | Converter Control | Converter Control | Converter Control | Converter Control |
| SBDEV977 | 0000067-63-0 | Converter Control | Converter Control | Converter Control | Converter Control | Converter Control |
| SBDEV977 | 0007732-18-5 | Converter Control | Converter Control | Converter Control | Converter Control | Converter Control |
| SBDEV977 | 0000109-60-4 | Converter Control | Converter Control | Converter Control | Converter Control | Converter Control |
| SBDEV977 | 0000111-42-2 | Converter Control | Converter Control | Converter Control | Converter Control | Converter Control |
| SBDEV977 | 0000141-43-5 | Converter Control | Converter Control | Converter Control | Converter Control | Converter Control |
| SBDEV979 | 0001333-86-4 | 77 | 30.3 | _110.9_ | 46.8 | _117.2_ |
| SBDEV979 | 0009004-36-8 | 14 | 5.5 | 20.2 | 8.5 | 21.3 |
| SBDEV979 | 0009002-88-4 | 5 | 2.0 | 7.2 | 3.0 | 7.6 |
| SBDEV979 | 0008002-74-2 | 5 | 2.0 | 7.2 | 3.0 | 7.6 |
| SBDEV979 | 0000128-37-0 | 60 | 23.6 | 86.4 | 36.5 | 91.3 |
| SBDEV979 | 0004098-71-9 | _1200_ | _472.0_ | _1728.0_ | _730.0_ | _1826.0_ |
| SBDEV979 | 0004744-11-0 | _2800_ | _1101.3_ | _4032.0_ | _1703.3_ | _4260.7_ |
| SBDEV979 | 0000120-93-4 | 15 | 5.9 | 21.6 | 9.1 | 22.8 |
| SBDEV979 | 0002390-43-2 | 65 | 25.6 | 93.6 | 39.5 | 98.9 |
| SBDEV979 | 0000077-90-7 | 0.10 | 0.04 | 0.14 | 0.06 | 0.15 |
| SBDEV979 | 0000126-73-8 | 0 | 0 | 0 | 0 | 0 |
| SBDEV979 | 0000111-62-6 | 22.7 | 8.92 | 32.7 | 19.9 | 34.5 |
| SBDEV979 | 0000077-94-1 | 52.8 | 20.8 | 76.0 | 46.2 | 80.3 |
| SBDEV979 | 0000071-23-8 | Converter Control | Converter Control | Converter Control | Converter Control | Converter Control |
| SBDEV979 | 0000064-17-5 | Converter Control | Converter Control | Converter Control | Converter Control | Converter Control |
| SBDEV979 | 0000141-78-6 | Converter Control | Converter Control | Converter Control | Converter Control | Converter Control |
| SBDEV979 | 0000067-63-0 | Converter Control | Converter Control | Converter Control | Converter Control | Converter Control |
| SBDEV979 | 0007732-18-5 | Converter Control | Converter Control | Converter Control | Converter Control | Converter Control |
| SBDEV979 | 0000109-60-4 | Converter Control | Converter Control | Converter Control | Converter Control | Converter Control |
| SBDEV980 | 0009004-36-8 | 14 | 5.5 | 20.2 | 8.5 | 21.3 |
| SBDEV980 | 0009002-88-4 | 5 | 2.0 | 7.2 | 3.0 | 7.6 |
| SBDEV980 | 0008002-74-2 | 5 | 2.0 | 7.2 | 3.0 | 7.6 |
| SBDEV980 | 0000128-37-0 | 64 | 25.2 | 92.2 | 38.9 | 97.4 |
| SBDEV980 | 0003815-20-1 | _230_ | 90.5 | _331.2_ | _139.9_ | _350.0_ |
| SBDEV980 | No CAS | _380_ | _149.5_ | _547.2_ | _231.2_ | _578.2_ |
| SBDEV980 | 0000104-88-1 | 14 | 5.5 | 20.2 | 8.5 | 21.3 |
| SBDEV980 | 0031274-51-8 | 0.3 | 0.1 | 0.4 | 0.2 | 0.5 |
| SBDEV980 | 0000092-92-2 | 7 | 2.8 | 10.1 | 4.3 | 10.7 |
| SBDEV980 | 0002920-38-9 | 5 | 2.0 | 7.2 | 3.0 | 7.6 |
| SBDEV980 | 0153531-70-5 | 5 | 2.0 | 7.2 | 3.0 | 7.6 |
| SBDEV980 | No CAS | 21 | 8.3 | 30.2 | 12.8 | 32.0 |
| SBDEV980 | 0003218-36-8 | 0.9 | 0.4 | 1.3 | 0.5 | 1.4 |
| SBDEV980 | 0004098-71-9 | _1300_ | _511.3_ | _1872.0_ | _790.8_ | _1978.2_ |
| SBDEV980 | 0004744-11-0 | _3000_ | _1180.0_ | _4320.0_ | _1825.0_ | _4565.0_ |
| SBDEV980 | 0000120-93-4 | 16 | 6.3 | 23.0 | 9.7 | 24.3 |
| SBDEV980 | 0002396-43-2 | 60 | 26.0 | 95.0 | 40.2 | _100.4_ |
| SBDEV980 | 0000077-90-7 | 0.11 | 0.04 | 0.16 | 0.07 | _0.17_ |
| SBDEV980 | 0000126-73-8 | 0 | 0 | 0 | 0 | _0_ |
| SBDEV980 | 0000111-62-6 | 24.0 | 9.45 | 34.5 | 14.6 | _36.5_ |
| SBDEV980 | 0000077-94-1 | 53.4 | 21.0 | 76.9 | 32.5 | _81.2_ |
| SBDEV980 | 0000071-23-8 | Converter Control | Converter Control | Converter Control | Converter Control | Converter Control |
| SBDEV980 | 0000064-17-5 | Converter Control | Converter Control | Converter Control | Converter Control | Converter Control |
| SBDEV980 | 0000141-78-6 | Converter Control | Converter Control | Converter Control | Converter Control | Converter Control |
| SBDEV980 | 0000067-63-0 | Converter Control | Converter Control | Converter Control | Converter Control | Converter Control |
| SBDEV980 | 0007732-18-5 | Converter Control | Converter Control | Converter Control | Converter Control | Converter Control |
| SBDEV980 | 0000109-60-4 | Converter Control | Converter Control | Converter Control | Converter Control | Converter Control |

Table 13 represents a hypothetical migration analysis calculated on the basis of worst-case scenarios. Two categories of cells in Table 13 are of particular note:
1. The cells containing underlined, italicized and bold font, wherein the worst-case calculation, expressed as a percentage of SML (or restriction), for a substance is over 100/o in one or more applications. As explained above, if the entirety of such a substance were to migrate from the packaging to the foodstuff, the migration limit would be exceeded. For these substances, the provision of ink and coating compositions according to the invention involves a determination of the true level of migration, by migration testing, to assess whether such substances in fact exceed the hypothetical limits, as explained below and in Table 14.
2. The cells marked as "Converter Control". As explained in Table 12, the concentration of volatile substances in a dried ink layer may depend on the process (in particular the drying process) applied by a downstream user of the ink, namely the convertor. According to the present invention, migration testing is preferably extended to encompass such substances. As noted in Table 14 below, none of these substances were detected in the migration testing conducted by the inventors.

In Table 13, a film having a dry coat weight of 2.0 g/m$^2$ is assumed. Calculation of the amount of a substance in the dried film assumes that any volatile material(s) or solvent(s) have been evaporated. The skilled person will appreciate that, in practice, there may be a residual amount of one or more volatile substances remaining in the dried film (because the actual amount may depend on the drying process effected under the control of the convertor, as explained above). Thus, in practice, the amount of a substance in the dried film as reported in Table 13 may be slightly lower than the values reported in the table. However, the skilled person will appreciate that where an amount (in wt %) of a substance in a dried film is expressed in Table 13, this corresponds to the maximum amount that could be present in the dried film, assuming that all volatiles are removed, because it is this maximum amount which is safety-critical for the method of the invention. In other words, basing the subsequent steps in the method on this maximum amount ensures the highest degree of food-safety.

Migration Testing

For any composition containing a substance which exhibits a worst case calculation (WCC) which exceeds the specific migration limit then, according to the present invention, the true level of migration is determined analytically by migration testing of the ink or coating composition in which the substance is contained. The true migration levels for volatile substances whose concentration in the final dried ink may be dependent on the downstream user (e.g. the convertor) are optionally also determined.

As will be understood in the art, the amount of substance that will migrate into a food is dependent on the chemistry of the food as well as contact times and temperatures. To simulate this, the inventors considered migration into 4 different food simulant/temperature/time scenarios that are relevant for the types of applications where the DFC inks can be used. Table 14 contains the results of the migration testing of the ink composition, in particular the results of the GC-MS analysis for each of the 4 different food simulant/temperature/time scenarios, namely the 10% ethanol test at 20° C., the 50% ethanol test at 20° C., the hot fill boiled water test and the 3% acetic acid test at 20° C.

Migration testing was performed as follows:

Printed substrates (with a dry coat weight of 2.0 g/m$^2$ for the printed layer) were placed into migration cells with the printed side of the samples facing into the cell. The cells were then filled with the required food simulants, sealed and stored for 10 days at 20° C. Thus, the food simulants are contacted with the printed surfaces in the migration cells. Though the print areas differed between each test, they remained a consistent 1:1 ratio of print surface area to simulant volume; 10 cm of print in contact with 10 mL of 10% ethanol; 50 cm$^2$ of print in contact with 50 mL of 50% ethanol; and 100 cm$^2$ of print in contact with 100 mL of 3% Acetic Acid. A control sample of unprinted substrate was also prepared in the same manner for each test simulant. All samples were tested in duplicate for reproducibility purposes.

After the 10 day incubation, the simulant was removed from the cells and the total volumes extracted with 2×10 mL of dichloromethane. A control sample of unprinted substrate was extracted in the same manner. The 20 mL dichloromethane was then concentrated down to 1 mL using a Buchi solvent evaporator using a temperature of 50° C. and a pressure between 60-80 bar. The 1 mL extract was then syringe filtered using a 0.2 µm PTFE syringe filter into a 2 mL GC vial. A known concentration of internal standard was then added to each vial.

For the hot fill boiled water test, 50 cm$^2$ of print was immersed in 50 ml of water at 100° C. then allowed to cool, which took approximately 1 hour. The water was then extracted with 2×10 mL dichloromethane and concentrated down in the exact same way as the test simulants mentioned above. This test was also carried out in duplicate.

The GC-MS used for analysis of these migration extracts was a Thermo ISQ 1300 with a CT splitless injection. The column used was a Thermo TG-5SILMS, 30 m, 0.25 mm internal diameter and 0.25 µm film thickness. The instrument parameters were as follows:

Injection temperature was constant at 280° C.;

GC Oven temperature programme (with a flow rate of 1.2 mL/min):

| Temp. ramp (° C./min) | Temp. (° C.) | Hold Time (min) |
|---|---|---|
| — | 60 | 4 |
| 40 | 200 | 0 |
| 40 | 300 | 0 |

MS parameters:

Temperature of the transfer line is 300° C. and the ion source temperature is 200° C.;

The scanned mass range for the method is 45-650 amu; and

Solvent delay before data acquisition is 3 minutes.

All data analysis for the migration test was done in the GC-MS full scan data. This means that any peaks seen were identified using library matches (internal and NIST libraries) and quantified against the response of the internal standard. The components identified from the migration tests were cross-checked against the data acquired from the raw material analysis to establish the source of some of the components seen to migrate.

The results of the migration testing allow calculation of the mg of substance migrating per m$^2$ of print, and hence allow the measured migration levels ($M_L$) to be correlated to, and contextualized within, the EU Cube exposure model (having a surface of 0.06 m$^2$ and containing 1 kg of food). The true migration levels $M_L$ may then be compared directly with the Specific Migration Limits (SML). In Table 14, analytically measured migration values are reported in the units of % of the SML; as such, a substance which is reported as having a value of 100% or more presents a food-contact risk.

Table 14 provides results of analytic testing for detectable materials in four of the inks described herein, namely the SBDEV976, SBDEV977, SBDEV979 and SBDEV980 ink compositions (Examples 4A-4D). For ease of reference, Table 14 incorporates the information from Table 13 regarding the relevant substances, their SML/restriction, the source of the SML/restriction, and the WCCs (expressed as a percentage of the SML) of each substance in the standard EU Cube model.

In Table 14, "ND" means not detected (defined as a signal to noise ratio of less than 3:1)

The measured value in this empirical migration testing should be below 100% of the SML for any given substance in order for an ink composition which contains that substance to be considered acceptable for unrestricted use in food contact applications, and in particular direct food contact applications.

TABLE 14

| Product containing substance | CAS No of substance | Name of substance | SML or Restriction (mg substance/ kg food) |
|---|---|---|---|
| SBDEV976 | 0009004-36-8 | cellulose acetate butyrate | 60 |
| SBDEV976 | 0009002-88-4 | polyethylene wax | 60 |
| SBDEV976 | 0008002-74-2 | waxes, refined, derived from petroleum based or synthetic hydrocarbon feedstocks, high viscosity | 60 |
| SBDEV976 | 0000128-37-0 | 2,6-Di-tert-butyl-p-cresol (=BHT) | 3 |
| SBDEV976 | 0000091-20-3 | Naphthalene | 0.01 |
| SBDEV976 | 0064742-94-5 | Solvent naphtha (petroleum), heavy arom. | 0.01 |
| SBDEV976 | 0004098-71-9 | IPDI (isophorone diisocyanate) | 1 |
| SBDEV976 | 0004744-11-0 | Propane, 1,1-dipropoxy- | 0.09 |
| SBDEV976 | 0000120-93-4 | 2-Imidazolidinone | 4.98 |
| SBDEV976 | 0002396-43-2 | 2,4,6-tripropyl-1,3,5-Trioxane | 0.09 |
| SBDEV976 | 0000071-23-8 | 1-propanol | 60 |
| SBDEV976 | 0000064-17-5 | ethanol | 60 |
| SBDEV976 | 0000141-78-6 | acetic acid, ethyl ester | 60 |
| SBDEV976 | 0000067-63-0 | 2-propanol | 60 |
| SBDEV976 | 0007732-18-5 | water | 60 |
| SBDEV976 | 0000109-60-4 | Acetic acid, propyl ester | 60 |
| SBDEV976 | 0000100-41-4 | Ethylbenzene | 0.6 |
| SBDEV976 | 0000077-90-7 | Tributyl acetyl citrate | 60 |
| SBDEV976 | 0000126-73-8 | Tributyl phosphate | 0.05 |
| SBDEV976 | 0000111-62-6 | Ethyl Oleate | 0.09 |
| SBDEV976 | 0000077-94-1 | Tributyl citrate | 0.05 |
| SBDEV977 | 0009004-36-8 | cellulose acetate butyrate | 60 |
| SBDEV977 | 0009002-88-4 | polyethylene wax | 60 |
| SBDEV977 | 0008002-74-2 | waxes, refined, derived from petroleum based or synthetic hydrocarbon feedstocks, high viscosity | 60 |
| SBDEV977 | 0000128-37-0 | 2,6-Di-tert-butyl-p-cresol (=BHT) | 3 |
| SBDEV977 | 0000102-71-6 | Triethanolamine | 0.05 |
| SBDEV977 | 0013481-50-0 | 2,4,6(1H,3H,5H)-Pyrimidinetrione, 5-(2,3-Dihydro-3-Oxo-1H-Isoindol-1-Ylidene)- | 0.09 |
| SBDEV977 | 0000067-52-7 | Barbituric acid | 0.09 |
| SBDEV977 | 0000085-41-6 | Phthalimide | 0.09 |
| SBDEV977 | 0004098-71-9 | IPDI (isophorone diisocyanate) | 1 |
| SBDEV977 | 0004744-11-0 | Propane, 1,1-dipropoxy- | 0.09 |
| SBDEV977 | 0000120-93-4 | 2-Imidazolidinone | 4.98 |
| SBDEV977 | 0002396-43-2 | 2,4,6-tripropyl-1,3,5-Trioxane | 0.09 |
| SBDEV977 | 0000093-83-4 | N,N-Bis(2-hydroxyethyl) oleamide | 0.09 |
| SBDEV977 | 0000071-23-8 | 1-propanol | 60 |
| SBDEV977 | 0000064-17-5 | ethanol | 60 |
| SBDEV977 | 0000141-78-6 | acetic acid, ethyl ester | 60 |
| SBDEV977 | 0000067-63-0 | 2-propanol | 60 |
| SBDEV977 | 0007732-18-5 | water | 60 |
| SBDEV977 | 0000109-60-4 | Acetic acid, propyl ester | 60 |
| SBDEV977 | 0000111-42-2 | Diethanolamine | 0.3 |
| SBDEV977 | 0000141-43-5 | 2-aminoethanol | 0.05 |
| SBDEV977 | 0000077-90-7 | Tributyl acetyl citrate | 60 |
| SBDEV977 | 0000126-73-8 | Tributyl phosphate | 0.05 |
| SBDEV977 | 0000111-62-6 | Ethyl Oleate | 0.09 |
| SBDEV977 | 0000077-94-1 | Tributyl citrate | 0.05 |
| SBDEV979 | 0001333-86-4 | carbon black | 60 |
| SBDEV979 | 0009004-36-8 | cellulose acetate butyrate | 60 |
| SBDEV979 | 0009002-88-4 | polyethylene wax | 60 |
| SBDEV979 | 0008002-74-2 | waxes, refined, derived from petroleum based or synthetic hydrocarbon feedstocks, high viscosity | 60 |
| SBDEV979 | 0000128-37-0 | 2,6-Di-tert-butyl-p-cresol (=BHT) | 3 |
| SBDEV979 | 0004098-71-9 | IPDI (isophorone diisocyanate) | 1 |
| SBDEV979 | 0004744-11-0 | Propane, 1,1-dipropoxy- | 0.09 |
| SBDEV979 | 0000120-93-4 | 2-Imidazolidinone | 4.98 |
| SBDEV979 | 0002396-43-2 | 2,4,6-tripropyl-1,3,5-Trioxane | 0.09 |
| SBDEV979 | 0000071-23-8 | 1-propanol | 60 |

TABLE 14-continued

| | | | |
|---|---|---|---|
| SBDEV979 | 0000064-17-5 | ethanol | 60 |
| SBDEV979 | 0000141-78-6 | acetic acid, ethyl ester | 60 |
| SBDEV979 | 0000067-63-0 | 2-propanol | 60 |
| SBDEV979 | 0007732-18-5 | water | 60 |
| SBDEV979 | 0000109-60-4 | Acetic acid, propyl ester | 60 |
| SBDEV979 | 0000077-90-7 | Tributyl acetyl citrate | 60 |
| SBDEV979 | 0000126-73-8 | Tributyl phosphate | 0.05 |
| SBDEV979 | 0000111-62-6 | Ethyl Oleate | 0.09 |
| SBDEV979 | 0000077-94-1 | Tributyl citrate | 0.05 |
| SBDEV980 | 0009004-36-8 | cellulose acetate butyrate | 60 |
| SBDEV980 | 0009002-88-4 | polyethylene wax | 60 |
| SBDEV980 | 0008002-74-2 | waxes, refined, derived from petroleum based or synthetic hydrocarbon feedstocks, high viscosity | 60 |
| SBDEV980 | 0000128-37-0 | 2,6-Di-tert-butyl-p-cresol (=BHT) | 3 |
| SBDEV980 | 0003815-20-1 | 4-Phenylbenzamide | 0.09 |
| SBDEV980 | No CAS | 2,4,6-Tris-Biphenyl-4-Yl-7H-Pyrrolo[2,3-D]Pyrimidine-5-Carboxylic Acid | 0.01 |
| SBDEV980 | 0000104-88-1 | 4-Chlorobenzaldehyde | 0.09 |
| SBDEV980 | 0031274-51-8 | 1,3,5-Triazine, 2,4,6-Tris([1,1'-Biphenyl]-4-Yl)- | 5 |
| SBDEV980 | 0000092-92-2 | 4-Phenylbenzoic Acid | 0.09 |
| SBDEV980 | 0002920-38-9 | 4-Phenylbenzonitrile | 0.09 |
| SBDEV980 | 0153531-70-5 | Di-Isopropyl-Succinyl-Succinate | 0.09 |
| SBDEV980 | No CAS | 2,4-Bis-Biphenyl-4-Yl-6-Methyl-[1,3]Pyrimidine | 0.01 |
| SBDEV980 | 0003218-36-8 | 4-Phenylbenzaldehyde | 0.09 |
| SBDEV980 | 0004098-71-9 | IPDI (isophorone diisocyanate) | 1 |
| SBDEV980 | 0004744-11-0 | Propane, 1,1-dipropoxy- | 0.09 |
| SBDEV980 | 0000120-93-4 | 2-Imidazolidinone | 4.98 |
| SBDEV980 | 0002396-43-2 | 2,4,6-tripropyl-1,3,5-Trioxane | 0.09 |
| SBDEV980 | 0000071-23-8 | 1-propanol | 60 |
| SBDEV980 | 0000064-17-5 | ethanol | 60 |
| SBDEV980 | 0000141-78-6 | Acetic acid, ethyl ester | 60 |
| SBDEV980 | 0000067-63-0 | 2-propanol | 60 |
| SBDEV980 | 0007732-18-5 | water | 60 |
| SBDEV980 | 0000109-60-4 | Acetic acid, propyl ester | 60 |
| SBDEV980 | 0000077-90-7 | Tributyl acetyl citrate | 60 |
| SBDEV980 | 0000126-73-8 | Tributyl phosphate | 0.05 |
| SBDEV980 | 0000111-62-6 | Ethyl Oleate | 0.09 |
| SBDEV980 | 0000077-94-1 | Tributyl citrate | 0.05 |

| Product Containing substance | CAS No of substance | Source of SML or restriction | Worst Case Calculation of migration in EU Cube model (as a percentage of SML) | Analytically measured migration (% SML) | | | |
|---|---|---|---|---|---|---|---|
| | | | | 10% EtOH 20° C. | 50% EtOH 20° C. | Hot fill boiled water | 3% acetic acid 20° C. |
| SBDEV976 | 0009004-36-8 | PR | 14 | ND | ND | ND | ND |
| SBDEV976 | 0009002-88-4 | PR | 5 | ND | ND | ND | ND |
| SBDEV976 | 0008002-74-2 | PR | 5 | ND | ND | ND | ND |
| SBDEV976 | 0000128-37-0 | PR | 65 | ND | ND | ND | ND |
| SBDEV976 | 0000091-20-3 | Default 10 ppb | 0.4 | ND | ND | ND | ND |
| SBDEV976 | 0064742-94-5 | SO | *170* | ND | ND | ND | ND |
| SBDEV976 | 0004098-71-9 | PR | *1300* | ND | ND | ND | ND |
| SBDEV976 | 0004744-11-0 | HA | *3000* | ND | ND | ND | ND |
| SBDEV976 | 0000120-93-4 | HA | 16 | ND | ND | ND | ND |
| SBDEV976 | 0002396-43-2 | HA | 61 | ND | ND | ND | ND |
| SBDEV976 | 0000071-23-8 | PR | Converter Control | ND | ND | ND | ND |
| SBDEV976 | 0000064-17-5 | PR | Converter Control | ND | ND | ND | ND |
| SBDEV976 | 0000141-78-6 | PR | Converter Control | ND | ND | ND | ND |
| SBDEV976 | 0000067-63-0 | PR | Converter Control | ND | ND | ND | ND |
| SBDEV976 | 0007732-18-5 | PR | Converter Control | ND | ND | ND | ND |
| SBDEV976 | 0000109-60-4 | SO | Converter Control | ND | ND | ND | ND |
| SBDEV976 | 0000100-41-4 | SO | Converter Control | ND | ND | ND | ND |
| SBDEV976 | 0000077-90-7 | PR | 0.12 | 0.24 | 0.078 | 0.067 | 0.528 |
| SBDEV976 | 0000126-73-8 | SO | 0 | ND | ND | ND | ND |
| SBDEV976 | 0000111-62-6 | HA | 24.0 | ND | 12.22 | ND | ND |
| SBDEV976 | 0000077-94-1 | SO | 55.2 | ND | ND | ND | 44 |
| SBDEV977 | 0009004-36-8 | PR | 15 | ND | ND | ND | ND |
| SBDEV977 | 0009002-88-4 | PR | 5 | ND | ND | ND | ND |
| SBDEV977 | 0008002-74-2 | PR | 5 | ND | ND | ND | ND |
| SBDEV977 | 0000128-37-0 | PR | 60 | ND | ND | ND | ND |

TABLE 14-continued

| | | | | | | | |
|---|---|---|---|---|---|---|---|
| SBDEV977 | 0000102-71-6 | PR | 2 | ND | ND | ND | ND |
| SBDEV977 | 0013481-50-0 | HA | _3800_ | ND | ND | ND | ND |
| SBDEV977 | 0000067-52-7 | HA | _1300_ | ND | ND | ND | ND |
| SBDEV977 | 0000085-41-6 | HA | _960_ | ND | ND | ND | 31.11 |
| SBDEV977 | 0004098-71-9 | PR | _1200_ | ND | ND | ND | ND |
| SBDEV977 | 0004744-11-0 | HA | _2800_ | ND | ND | ND | ND |
| SBDEV977 | 0000120-93-4 | HA | _15_ | ND | ND | ND | ND |
| SBDEV977 | 0002396-43-2 | HA | 67 | ND | ND | ND | ND |
| SBDEV977 | 0000093-83-4 | HA | 69 | ND | ND | ND | ND |
| SBDEV977 | 0000071-23-8 | PR | Converter Control | ND | ND | ND | ND |
| SBDEV977 | 0000064-17-5 | PR | Converter Control | ND | ND | ND | ND |
| SBDEV977 | 0000141-78-6 | PR | Converter Control | ND | ND | ND | ND |
| SBDEV977 | 0000067-63-0 | PR | Converter Control | ND | ND | ND | ND |
| SBDEV977 | 0007732-18-5 | PR | Converter Control | ND | ND | ND | ND |
| SBDEV977 | 0000109-60-4 | SO | Converter Control | ND | ND | ND | ND |
| SBDEV977 | 0000111-42-2 | SO | Converter Control | ND | ND | ND | ND |
| SBDEV977 | 0000141-43-5 | PR | Converter Control | ND | ND | ND | ND |
| SBDEV977 | 0000077-90-7 | PR | 0.11 | 0.208 | 7E−06 | 0.1 | 0.55 |
| SBDEV977 | 0000126-73-8 | SO | 638.4 | ND | 46 | **_200*_** | **_178*_** |
| SBDEV977 | 0000111-62-6 | HA | 24 | ND | 11.11 | _ND_ | _ND_ |
| SBDEV977 | 0000077-94-1 | SO | 53.2 | ND | ND | ND | 20 |
| SBDEV979 | 0001333-86-4 | PR | 77 | ND | ND | ND | ND |
| SBDEV979 | 0009004-36-8 | PR | 14 | ND | ND | ND | ND |
| SBDEV979 | 0009002-88-4 | PR | 5 | ND | ND | ND | ND |
| SBDEV979 | 0008002-74-2 | PR | 5 | ND | ND | ND | ND |
| SBDEV979 | 0000128-37-0 | PR | 60 | ND | ND | ND | ND |
| SBDEV979 | 0004098-71-9 | PR | _1200_ | ND | ND | ND | ND |
| SBDEV979 | 0004744-11-0 | HA | _2800_ | ND | ND | ND | ND |
| SBDEV979 | 0000120-93-4 | HA | _15_ | ND | ND | ND | ND |
| SBDEV979 | 0002396-43-2 | HA | 65 | ND | ND | ND | ND |
| SBDEV979 | 0000071-23-8 | PR | Converter Control | ND | ND | ND | ND |
| SBDEV979 | 0000064-17-5 | PR | Converter Control | ND | ND | ND | ND |
| SBDEV979 | 0000141-78-6 | PR | Converter Control | ND | ND | ND | ND |
| SBDEV979 | 0000067-63-0 | PR | Converter Control | ND | ND | ND | ND |
| SBDEV979 | 0007732-18-5 | PR | Converter Control | ND | ND | ND | ND |
| SBDEV979 | 0000109-60-4 | SO | Converter Control | ND | ND | ND | ND |
| SBDEV979 | 0000077-90-7 | PR | 0.10 | 0.362 | 0.072 | 0.055 | 0.488 |
| SBDEV979 | 0000126-73-8 | SO | 0 | ND | ND | ND | ND |
| SBDEV979 | 0000111-62-6 | HA | 22.2 | ND | ND | ND | ND |
| SBDEV979 | 0000077-94-1 | SO | 52.8 | ND | ND | ND | 22 |
| SBDEV980 | 0009004-36-8 | PR | 14 | ND | ND | ND | ND |
| SBDEV980 | 0009002-88-4 | PR | 5 | ND | ND | ND | ND |
| SBDEV980 | 0008002-74-2 | PR | 5 | ND | ND | ND | ND |
| SBDEV980 | 0000128-37-0 | PR | 64 | ND | ND | ND | ND |
| SBDEV980 | 0003815-20-1 | HA | _230_ | ND | ND | ND | ND |
| SBDEV980 | No CAS | Default 10 ppb | _380_ | ND | ND | ND | ND |
| SBDEV980 | 0000104-88-1 | HA | 14 | ND | ND | ND | ND |
| SBDEV980 | 0031274-51-8 | HA | 0.3 | ND | ND | ND | ND |
| SBDEV980 | 0000092-92-2 | HA | 7 | ND | ND | ND | ND |
| SBDEV980 | 0002920-38-9 | HA | 5 | ND | ND | ND | ND |
| SBDEV980 | 0153531-70-5 | HA | 5 | ND | ND | ND | ND |
| SBDEV980 | No CAS | Default 10 ppb | 21 | ND | ND | ND | ND |
| SBDEV980 | 0003218-36-8 | HA | 0.9 | ND | ND | ND | ND |
| SBDEV980 | 0004098-71-9 | PR | _1300_ | ND | ND | ND | ND |
| SBDEV980 | 0004744-11-0 | HA | _3000_ | ND | ND | ND | ND |
| SBDEV980 | 0000120-93-4 | HA | _16_ | ND | ND | ND | ND |
| SBDEV980 | 0002396-43-2 | HA | 66 | ND | ND | ND | ND |
| SBDEV980 | 0000071-23-8 | PR | Converter Control | ND | ND | ND | ND |
| SBDEV980 | 0000064-17-5 | PR | Converter Control | ND | ND | ND | ND |
| SBDEV980 | 0000141-78-6 | PR | Converter Control | ND | ND | ND | ND |

TABLE 14-continued

| | | | | | | | | |
|---|---|---|---|---|---|---|---|---|
| SBDEV980 | 0000067-63-0 | PR | Converter Control | ND | ND | ND | ND | |
| SBDEV980 | 0007732-18-5 | PR | Converter Control | ND | ND | ND | ND | |
| SBDEV980 | 0000109-60-4 | SO | Converter Control | ND | ND | ND | ND | |
| SBDEV980 | 0000077-90-7 | PR | | 0.11 | 0.387 | 0.068 | 0.0233 | 0.397 |
| SBDEV980 | 0000126-73-8 | SO | | 0 | ND | ND | ND | ND |
| SBDEV980 | 0000111-62-6 | HA | | 24.0 | ND | ND | ND | ND |
| SBDEV980 | 0000077-94-1 | SO | | 53.4 | ND | ND | ND | 36 |

The results of the migration testing in Table 14 demonstrate that the only ink composition containing a substance having a true migration value which exceeds the specific migration limit (SML) of the standard EU Cube model is SBDEV977 (Example 4A), as shown by the asterisks in the table. Tributyl phosphate (which was only detected in the yellow ink) shows migration values above the specific migration limit, i.e. migration values of 200% of SML in the hot filled boiled water test and 178% of SML in the 3% acetic acid at 20° C. test.

The empirical evidence of true migration levels in Table 14 therefore informs the selection of the inks and their end applications. The inks SBDEV976, SBDEV979 and SBDEV980 contain no substances for which the migration limit exceeds the SML of the standard EU Cube model, and are therefore acceptable for direct food contact in that packaging scenario. However, in order for the yellow ink (SBDEV977) to be acceptable on packaging for food contact (and in particular direct food contact), the use of the ink needs to be restricted in the final application, and in particular the coverage of the packaging surface(s) with the ink needs to be restricted. The degree of restriction can be calculated using the different exposure scenarios:

Application 1 (Yoghurt lids): As explained above, the maximum exposure in this scenario is approximately 39% of the exposure in the EU Cube model. As such, the empirical migration level for tributyl phosphate in this packaging scenario is 78% (39% of 200%) in the hot filled boiled water test and 69% (39% of 178%) in the 3% acetic acid at 20° C. test. In other words, the true migration level is less than the SML (i.e. less than 100% of the SML) in this packaging scenario and the ink is safe for food contact. As such, no restriction on the use of SBDEV977 ink is required when used to print the inside of yoghurt lids.

Application 2 (Wrap covering cheese; (250 g cheese, 11 cm×3.5 cm)): As explained above, the maximum exposure in this scenario is 144% of the exposure in the EU Cube model. The highest measured migration value of tributyl phosphate was 200%, and hence in this packaging scenario, the true migration value is 288% (144% of 200%) of the SML. In other words, the true migration value exceeds the SML, and therefore this ink must be restricted in use. However, this result does not mean that the ink can never be used in this packaging scenario, merely that its use must be restricted. Given that the exposure scenario is modelled on the basis of 100% ink coverage of the relevant surfaces in the packaging, the migration testing result means that the ink can still be used, but with a reduced coverage of the surfaces. Thus, in order for the migration value to tall below 100% of the SML, the SBDEV977 ink can only be used when its coverage of the relevant surfaces is less than 34% ((100/288)×100=−34% (rounded down to 2 significant figures).

Application 3 (Coffee capsules): As explained above, the maximum exposure in this scenario is between 61% and 152% of the exposure in the EU Cube model. The highest measured migration value of tributyl phosphate was 200%, and hence at the upper end of the exposure range in this packaging scenario, the true migration value is 304% (152% of 200%) of the SML, i.e. the true migration value exceeds the SML and therefore this ink must be restricted in use. In order for the migration value to be fall below 100% of the SML, the SBDEV977 ink can only be used when its coverage of the relevant surfaces is less than 32% ((100/304)×100=32% (rounded down to 2 significant figures)).

EU Cube model: because the empirical migration level exceeds the SML in this exposure scenario, the ink should not be used at 100% coverage of the relevant surfaces in packaging types which correspond to this model. In order for the migration value to be fall below 100% of the SML, the SBDEV977 ink can only be used when its coverage of the relevant surfaces is less than 50% ((100/200)×100=50%).

Therefore, it can be concluded from the empirical migration analysis that all of the four inks tested (Examples 4A to 4D) are adequate for food contact applications, as long as the coverage of the yellow ink is restricted to less than 32% in coffee capsules applications and less than 34% in cheese applications (250 g cheese, 11 cm×3.5 cm).

The invention claimed is:

1. A method of providing or identifying one or more ink or coating composition(s) suitable for food contact, said method comprising the steps of:
   (i) providing one or more colourant(s);
   (ii) identifying the substances and any impurities in said colourant(s), wherein said identification comprises subjecting said colourant(s) to an extraction test;
   (iii) establishing a specific migration limit (SML) for each of the substances identified in step (ii);
   (iv) formulating said one or more colourant(s) into said ink or coating composition, and calculating the proportion of each of the substances identified in step (ii) which is present in a finished printed layer derived from said ink or coating composition;
   (v) performing a worst-case calculation by assuming that 100% of each of the substances identified in step (ii) migrates to a foodstuff when contacted with a finished printed layer derived from said ink or coating composition;
   (vi) evaluating whether said worst-case calculation in step (v) for each of the substances identified in step (ii) satisfies the criterion of being equal to or greater than the specific migration limit (SML) from step (iii), and if said criterion is satisfied for any of said substances then subjecting said ink or coating composition to migration testing;

(vii) empirically determining by chemical analysis the migration level (ML) of each of said substances identified in step (ii) in one or more migration test(s);

(viii) evaluating whether the migration level (ML) measured empirically in step (vii) for each of said substances in said ink or coating composition satisfies the criterion of being less than the specific migration limit (SML) established for that substance in step (iii), (ix) selecting as an ink or coating composition suitable for food contact those ink or coating composition(s) for which every substance contained therein satisfies the criterion in step (viii).

2. A method according to claim 1 which is a method for identifying a plurality of ink or coating compositions suitable for food contact wherein said plurality of ink or coating compositions constitute a set.

3. A method according to claim 1 wherein said colourant is a commercially available product having one or more impurities declared by the manufacturer thereof.

4. A method according to claim 1 wherein one or more of the specific migration limit(s) in step (iii) is stipulated by regional regulations for food contact, selected from one or more of: the EU Plastics Regulation No. 10/2011; Swiss Ordinance on Materials and Articles 817.023.21 of the Food Safety and Veterinary Office of the Swiss Federal Department of Home Affairs; and US FDA Regulation 178.3297; and Chinese Regulation GB 9685-2008 and its subsequent updates.

5. A method according to claim 1 wherein one or more of the specific migration limit(s) in step (iii) is established by a hazard assessment using the Threshold of Toxicological Concern approach developed by the EFSA, or the EFSA and WHO.

6. A method according to claim 5 wherein the hazard assessment comprises establishing if the substance identified in step (ii) is genotoxic using VEGA QSAR (version 1.1.5) prediction models.

7. A method according to claim 1 wherein said specific migration limit(s) in step (iii) is established with reference to the standard EU Cube (10 cm$^3$) exposure model.

8. A method according to claim 1 wherein said worst-case calculation in step (v) is performed on the basis of one or more food contact exposure models, selected from the standard EU Cube (10 cm$^3$) exposure model, a yoghurt pot lid exposure model, a cheese packaging cylinder exposure model, and a coffee capsule frusto-conical exposure model.

9. A method according to claim 1 wherein said migration test in step (vii) comprises subjecting the ink or coating composition to one or more of a food simulant test selected from (a) the 10% ethanol test at 20° C., (b) the 50% ethanol test at 20° C., (c) the hot fill boiled water test and (d) the 3% acetic acid test at 20° C.

10. A method according to claim 1 further comprises the following steps subsequent to step (ix):

(xi) defining a food contact packaging surface onto which said ink composition(s) are to be disposed and calculating the area $A_{P-MAX}$ of said surface which corresponds to 100% coverage of said surface with said ink or coating composition(s);

(xii) defining an area $A_M$ which is the surface area of food contact in the exposure model on the basis of which said specific migration limits (SML) have been established in step (iii);

(xiii) calculating an adjusted migration level ($M_{L-A}$) which is specific to the food contact packaging surface defined in step (xi) wherein $M_{L-A}=M_L \times A_{P-MAX}/A_M$;

(xiv) selecting one or more ink or coating composition(s) suitable for unrestricted use on said food contact packaging surface if the $M_{L-A}$ values of all substances in said composition(s) is less than said SML(s).

11. A method according to claim 1 wherein said the ink or coating composition further comprises one or more diluents and/or one or more additives additional to said colourant(s), and wherein said method comprises the steps of:

(i) providing one or more colourant(s), one or more additive(s) and one or more diluent(s);

(ii) identifying the substances and any impurities in said colourant(s), additive(s) and diluent(s);

(iii) establishing a specific migration limit (SML) for each of the substances identified in step (ii);

(iv) formulating said one or more colourant(s) additive(s) and diluent(s) into said ink or coating composition, and calculating the proportion of each of the substances identified in step (ii) which is present in a finished printed layer derived from said ink or coating composition;

(v) performing a worst-case calculation by assuming that 100% of each of the substances identified in step (ii) migrates to a foodstuff when contacted with a finished printed layer derived from said ink or coating composition;

(vi) evaluating whether said worst-case calculation in step (v) for each of the substances identified in step (ii) satisfies the criterion of being equal to or greater than the specific migration limit (SML) from step (iii), and if said criterion is satisfied for any of said substances then subjecting said ink or coating composition to migration testing;

(vii) empirically determining by chemical analysis the migration level (ML) of each of said substances identified in step (ii) in one or more migration test(s);

(viii) evaluating whether the migration level (ML) measured empirically in step (vii) for each of said substances in said ink or coating composition satisfies the criterion of being less than the specific migration limit (SML) established for that substance in step (iii), (ix) selecting as an ink or coating composition suitable for food contact those ink or coating composition(s) for which every substance contained therein satisfies the criterion in step (viii).

12. A method according to claim 11 wherein said restricted application conditions are selected from a minimum duration of drying and/or a minimum temperature of drying of said ink or coating composition after application to a substrate, particularly wherein the said one or more substance(s) which fail the criterion in step (viii) are selected from diluents and other volatile substances present in said composition.

13. A method according to claim 1 wherein said method further comprises the step of evaluating the colour characteristics of a printed layer derived from said ink or coating composition(s) from step (vii), by measuring the L*a*b* colour parameters in the CIELAB (1976) colour space.

14. A method according to claim 13 which is a method for identifying a plurality of ink compositions suitable for food contact wherein said plurality of ink compositions constitute an ink set, wherein the method further comprises calculating the colour gamut of the ink set from the L*a*b* colour parameters.

15. A method according to claim 14 further comprising selecting ink compositions to provide an ink set which exhibits a gamut value which is at least 400% higher than that of an ink set formulated with iron oxide pigments.

16. A method according to claim 1 wherein said one or more ink or coating composition(s) contain a plurality of colourants, preferably comprising two or more of yellow, cyan, red and black.

17. A method according to claim 1 wherein each of said one or more colourant(s) are organic colourants.

18. A method according to claim 1 wherein said one or more ink or coating composition(s) are solvent-based.

19. A method according to claim 1 wherein said food contact is direct food contact.

20. A method of printing a substrate with one or more ink or coating composition(s) suitable for food contact, said method comprising the method defined in claim 1 and subsequently further comprising printing said one or more ink or coating composition(s) onto a substrate.

21. A method of packaging a foodstuff wherein a food contact ink is disposed in or on the packaging, said method comprising the method defined in claim 1 and further comprising the step of packaging said foodstuff with the printed substrate.

22. A method according to claim 20 wherein said one or more ink or coating composition(s) are in direct contact with said foodstuff.

23. A method according to claim 1, further comprising a step (x) selecting those ink or coating composition(s) containing one or more substance(s) which fail the criterion in step (viii) to be an ink or coating composition suitable for food contact only in restricted quantities.

24. A method according to claim 9, wherein a plurality of migration tests selected from tests (a) to (d) are conducted in which case the migration level (ML) is defined as the highest migration level measured in any of said plurality of migration tests.

25. A method according to claim 10, further comprising a step (xv) selecting one or more ink or coating composition(s) suitable for restricted use on said food contact packaging surface if the $M_{L-A}$ value of any substance in said composition(s) is equal to or greater than said SML(s), wherein said restricted use is defined by a coverage factor $C_F$, wherein $C_F=(100/M_{L-A})\times 100$, wherein said coverage factor $C_F$ is the maximum fraction of said food contact packaging surface area which can be covered by said one or more ink or coating composition(s) suitable for restricted use.

26. A method according to claim 11, further comprising a step (x) selecting those ink or coating composition(s) containing one or more substance(s) which fail the criterion in step (viii) to be an ink or coating composition suitable for food contact only in restricted quantities or under restricted application conditions.

27. A method according to claim 23 further comprises the following steps subsequent to step (x):
(xi) defining a food contact packaging surface onto which said ink composition(s) are to be disposed and calculating the area $A_{P-MAX}$ of said surface which corresponds to 100% coverage of said surface with said ink or coating composition(s);
(xii) defining an area $A_M$ which is the surface area of food contact in the exposure model on the basis of which said specific migration limits (SML) have been established in step (iii);
(xiii) calculating an adjusted migration level ($M_{L-A}$) which is specific to the food contact packaging surface defined in step (xi) wherein $M_{L-A}=ML\times A_{P-MAX}/A_M$; and
(xiv) selecting one or more ink or coating composition(s) suitable for unrestricted use on said food contact packaging surface if the $M_{L-A}$ values of all substances in said composition(s) is less than said SML(s).

28. A method according to claim 27, further comprising a step (xv) selecting one or more ink or coating composition(s) suitable for restricted use on said food contact packaging surface if the $M_{L-A}$ value of any substance in said composition(s) is equal to or greater than said SML(s), wherein said restricted use is defined by a coverage factor $C_F$, wherein $C_F=(100/M_{L-A})\times 100$, wherein said coverage factor $C_F$ is the maximum fraction of said food contact packaging surface area which can be covered by said one or more ink or coating composition(s) suitable for restricted use.

* * * * *